United States Patent
Mou et al.

(10) Patent No.: US 11,666,234 B2
(45) Date of Patent: Jun. 6, 2023

(54) BLOOD PRESSURE MEASUREMENT MODULE

(71) Applicant: MICROJET TECHNOLOGY CO., LTD., Hsinchu (TW)

(72) Inventors: Hao-Jan Mou, Hsinchu (TW);
Ching-Sung Lin, Hsinchu (TW);
Wen-Yang Yang, Hsinchu (TW);
Yung-Lung Han, Hsinchu (TW);
Chi-Feng Huang, Hsinchu (TW);
Chang-Yen Tsai, Hsinchu (TW);
Wei-Ming Lee, Hsinchu (TW)

(73) Assignee: MICROJET TECHNOLOGY CO., LTD., Hsinchu (TW)

( * ) Notice: Subject to any disclaimer, the term of this patent is extended or adjusted under 35 U.S.C. 154(b) by 353 days.

(21) Appl. No.: 17/034,346

(22) Filed: Sep. 28, 2020

(65) Prior Publication Data

US 2021/0127987 A1    May 6, 2021

(30) Foreign Application Priority Data

Oct. 31, 2019 (TW) .................. 108139584
Nov. 7, 2019 (TW) .................. 108140537
Mar. 3, 2020 (TW) .................. 109106975
Mar. 3, 2020 (TW) .................. 109106976

(51) Int. Cl.
*A61B 5/0235*        (2006.01)
*G01L 9/00*          (2006.01)
*A61B 5/00*          (2006.01)

(52) U.S. Cl.
CPC .......... *A61B 5/0235* (2013.01); *A61B 5/0004* (2013.01); *A61B 5/0022* (2013.01); *G01L 9/0041* (2013.01); *A61B 5/681* (2013.01); *A61B 5/6898* (2013.01)

(58) Field of Classification Search
CPC ... A61B 5/0235; A61B 5/0004; A61B 5/0022; A61B 5/681; A61B 5/6898; A61B 5/022; G01L 9/0041; G01L 19/0007
USPC .......................................... 600/498
See application file for complete search history.

(56) References Cited

U.S. PATENT DOCUMENTS

2006/0195035 A1*  8/2006  Sun ................. A61B 5/022
                                                    600/503

* cited by examiner

*Primary Examiner* — Daniel L Cerioni
*Assistant Examiner* — Jonathan E. Cooper
(74) *Attorney, Agent, or Firm* — McClure, Qualey & Rodack, LLP

(57) ABSTRACT

A blood pressure measurement module includes a base, a valve plate, a top cover, a micro pump, a driving circuit board, and a pressure sensor. The valve plate is disposed between the base and the top cover. The micro pump is in the base. The pressure sensor is disposed on the driving circuit board. An inlet channel of the top cover and the pressure sensor are connected to a gas bag. The micro pump operates to inflate the gas bag to press the skin of a user. The pressure sensor detects a pressure change in the gas bag so as to detect the blood pressure of the user.

20 Claims, 31 Drawing Sheets

BLOOD PRESSURE MEASUREMENT MODULE

CROSS-REFERENCES TO RELATED APPLICATIONS

This non-provisional application claims priority under 35 U.S.C. § 119(a) to Patent Application No. 108139584 filed in Taiwan, R.O.C. on Oct. 31, 2019, Patent Application No. 108140537 filed in Taiwan, R.O.C. on Nov. 7, 2019, Patent Application No. 109106975 filed in Taiwan, R.O.C. on Mar. 3, 2020, and Patent Application No. 109106976 filed in Taiwan, R.O.C. on Mar. 3, 2020, the entire contents of which are hereby incorporated by reference.

BACKGROUND

Technical Field

The present disclosure relates to a blood pressure measurement module. In particular, to a blood pressure measurement module that is ultra-thin and can be combined with a wearable electronic device or a portable device.

Related Art

In recent years, awareness of personal health care has gradually increased so that the need of regularly monitoring the self-health condition has been generated. However, since most of the instruments for examining the body health condition are fixed at their corresponding places, a person has to go to a medical service station or a hospital to obtain a health examination. Even if there are already some detection devices for household uses on the market, sizes of these devices are still too large to be carried easily. In the current efficiency-pursuing society, these detection devices are hard to meet the needs of users.

Among the various health related indexes, the most representative one should be the blood pressure. The blood vessels in one's body are like roads spreading all over the body. Thus, the blood pressure is just like the road conditions, and the condition of the blood delivery can be understood through the blood pressure. If anything happens to the body, the blood pressure will reflect it clearly.

In view of these, how to provide a device capable of accurately measuring the blood pressure of a user at any time and can be combined with a wearable electronic device or a portable electronic device such that the user can quickly check the blood pressure anytime and anywhere with the device is an issue.

SUMMARY

One object of the present disclosure is providing a blood pressure measurement module that can be combined with a portable device or a wearable electronic device, so that a user can carry the module conveniently and can measure the blood pressure anytime and anywhere.

A general embodiment of the present disclosure provides a blood pressure measurement module including a base, a valve plate, a top cover, a micro pump, a driving circuit board, and a pressure sensor. The base has a valve loading area, an accommodating trough area, a gas inlet hole, and an insertion hole. The valve loading area and the accommodation trough area are respectively disposed on different surfaces of the base. The gas inlet hole and the insertion hole are in communication with the accommodation trough area. A first recessed receiving chamber is disposed on the valve loading area, and a plurality of first through holes penetrate an inner wall of the first recessed receiving chamber. A first protruding structure extends from the first recessed receiving chamber. An inner wall of the accommodation trough area is recessed to form a gas collection chamber, and the gas collection chamber is in communication with the first through holes. The valve plate is disposed and loaded on the valve loading area. The valve plate comprises a valve hole corresponding to the first protruding structure. The top cover comprises an inlet channel and a discharge hole spaced apart from each other. The top cover has an assembling surface covering the valve plate. A portion of the assembling surface corresponding to the inlet channel is recessed to form an inlet chamber, and the inlet chamber is in communication with the inlet channel. A portion of the assembling surface corresponding to the discharge hole is recessed to form a discharge chamber, and the discharge chamber is in communication with the discharge hole. A communication channel is disposed between the inlet chamber and the discharge chamber. A second protruding structure extends from the discharge chamber, and the discharge hole is opened at a center portion of the second protruding structure, so that the valve plate and the second protruding structure normally abut against each other to have a pre-force action and to close the discharge hole. The inlet channel is connected to a gas bag for blood pressure measurement. The micro pump is disposed in the accommodation trough area to cover the gas collection chamber. The driving circuit board covers the accommodation trough area. The driving circuit board is configured to provide a driving signal for the micro pump so as to control an operation of the micro pump. The pressure sensor is disposed on the driving circuit board and electrically connected to the driving circuit board. The pressure sensor is in the insertion hole of the base, and the pressure sensor is connected to the gas bag through the top cover for gas pressure detection. The operation of the micro pump is controlled by the driving circuit board for a gas transmission, so that a gas outside the base is guided into the accommodation trough area through the gas inlet hole, and the gas is continuously guided to and converged in the gas collection chamber by the micro pump, so that the gas is configured to push the valve hole of the valve plate and detach the valve hole from the first protruding structure, thereby the gas is allowed to pass through the valve hole so as to be continuously guided into the inlet channel of the top cover and collected in the gas bag, whereby the gas is configured to inflate the gas bag and presses skin of a user, so that a blood pressure of the user is allowed to be measured through the pressure sensor.

BRIEF DESCRIPTION OF THE DRAWINGS

The disclosure will become more fully understood from the detailed description given herein below for illustration only, and thus not limitative of the disclosure, wherein.

DETAILED DESCRIPTION

The present disclosure will now be described more specifically with reference to the following embodiments. It is to be noted that the following descriptions of different embodiments of this disclosure are presented herein for purpose of illustration and description only, and it is not intended to limit the scope of the present disclosure.

Figure 1:
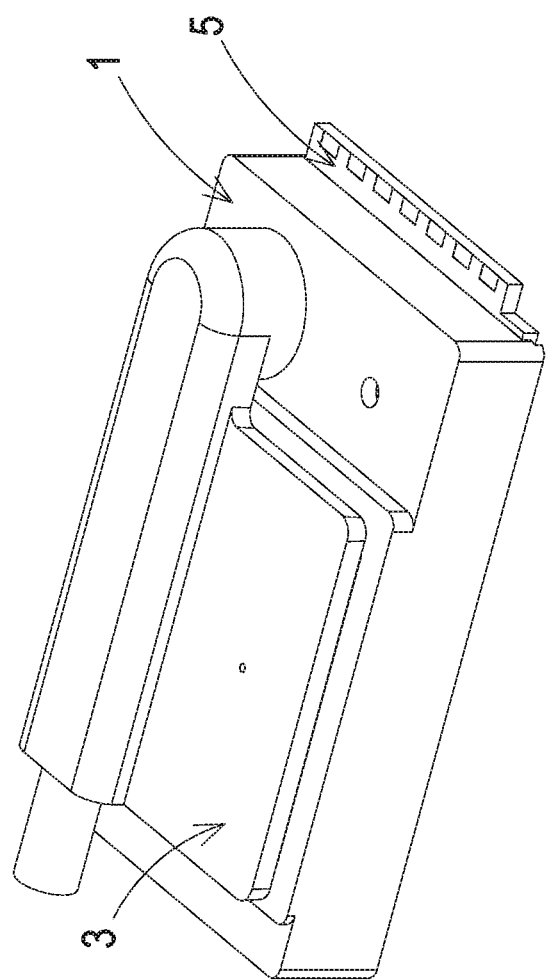
FIG. 1 illustrates a schematic perspective view of a blood pressure measurement module according to an exemplary embodiment of the present disclosure.
Figure 2A:
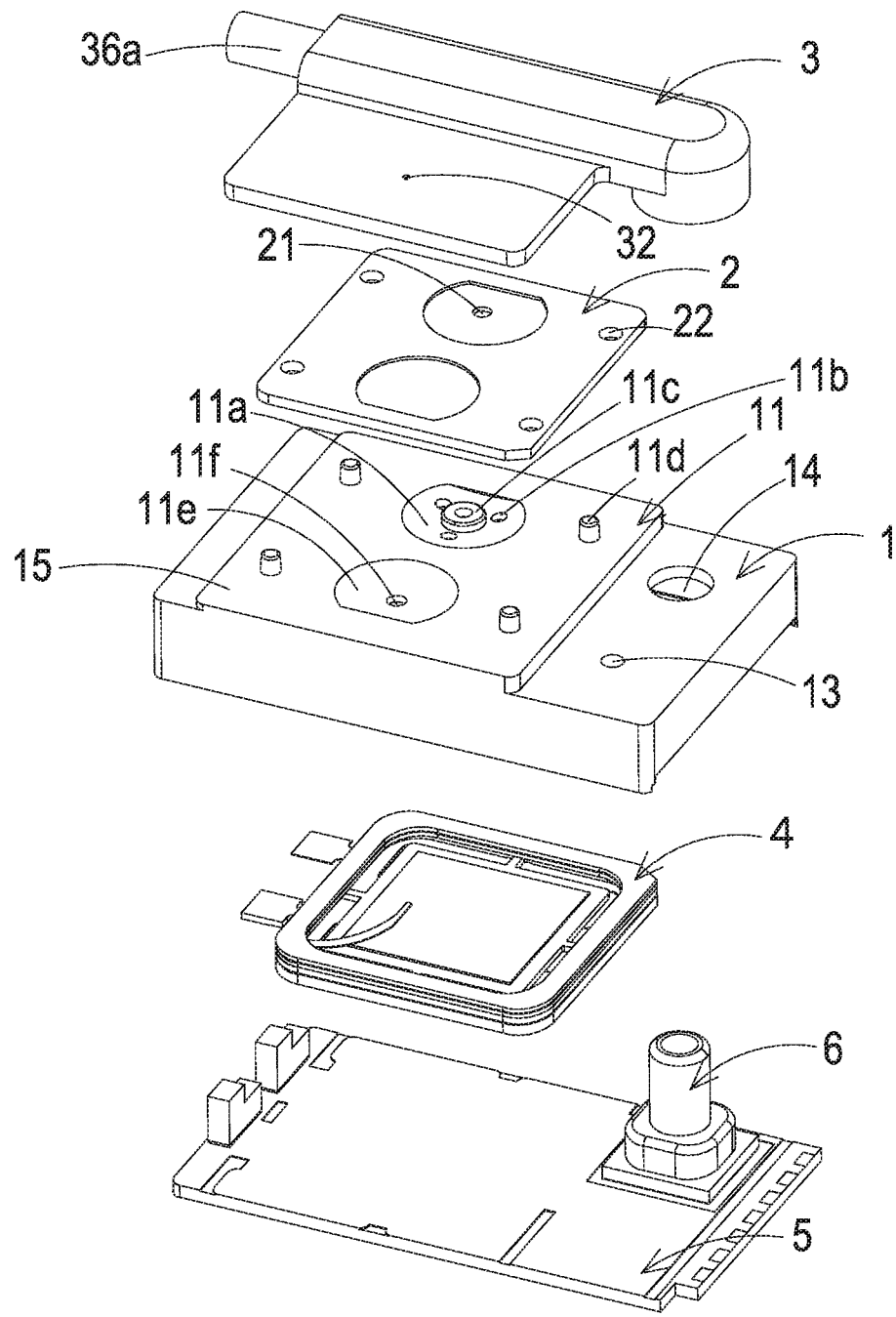
FIG. 2A illustrates a front exploded view of the blood pressure measurement module of the exemplary embodiment.
Figure 2B:
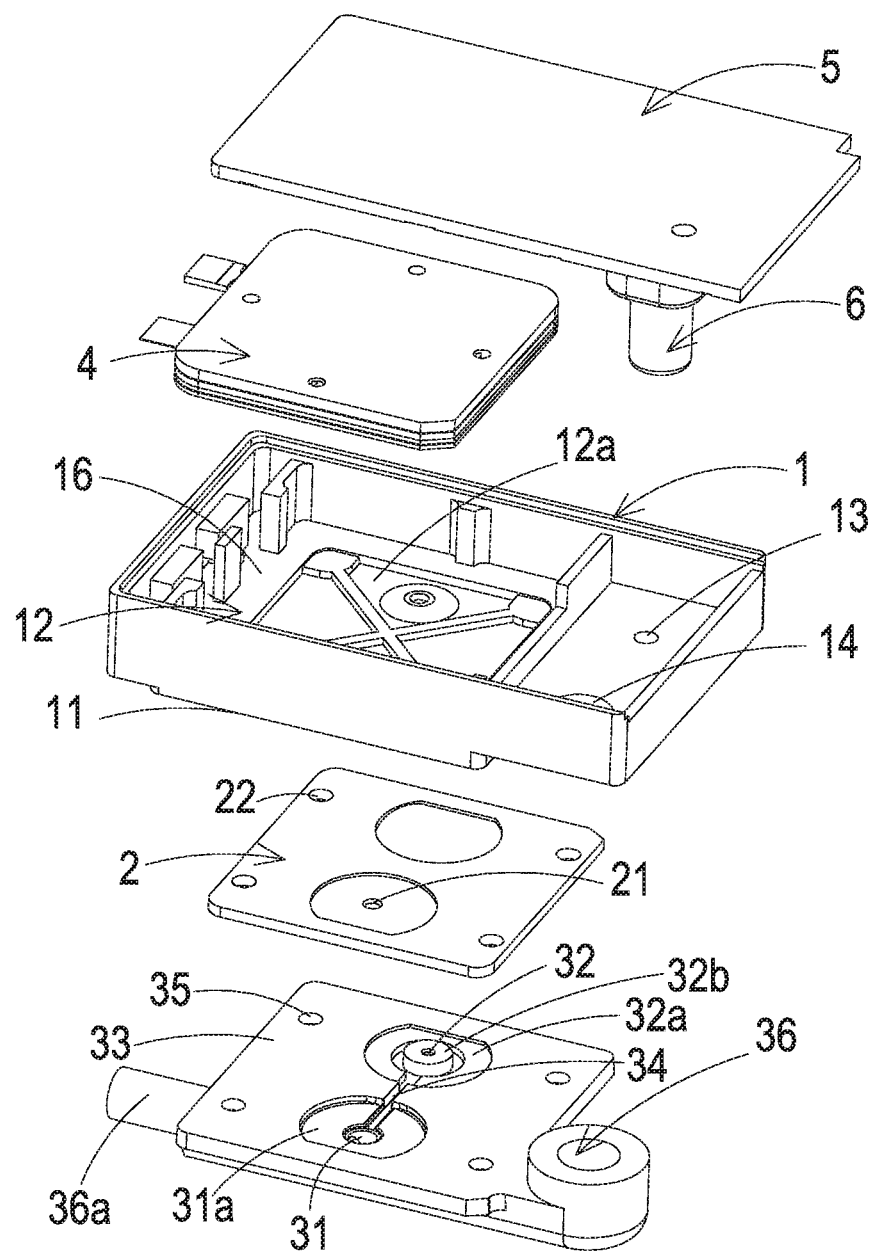
FIG. 2B illustrates a rear exploded view of the blood pressure measurement module of the exemplary embodiment.
Figure 3:
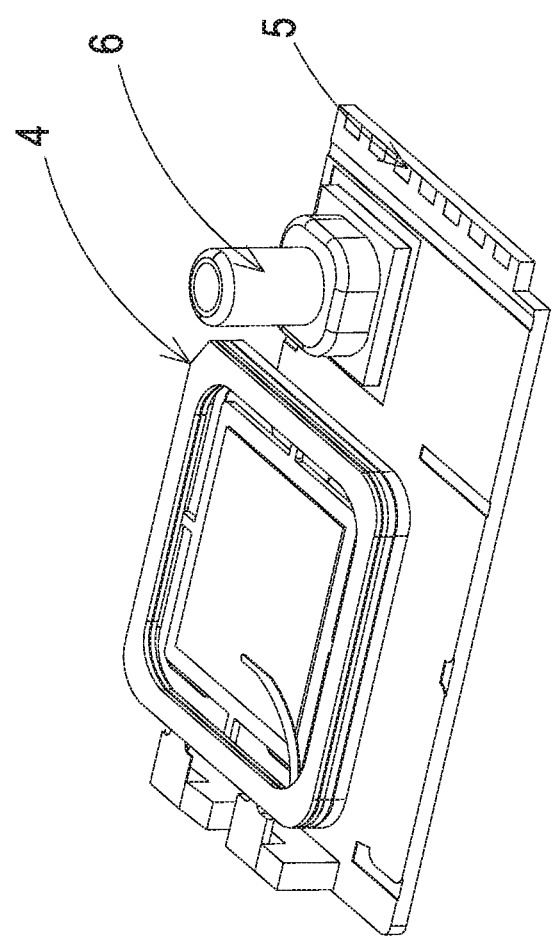
FIG. 3 illustrates a schematic perspective view showing that the pressure sensor is disposed on the driving circuit board, according to the blood pressure measurement module of the exemplary embodiment.

Please refer to FIG. 1, FIG. 2A, and FIG. 2B. A blood pressure measurement module is provided and includes a base 1, a valve plate 2, a top cover 3, a micro pump 4, a driving circuit board 5, and a pressure sensor 6. The base 1, the valve plate 2, the top cover 3, the micro pump 4, the driving circuit board 5, and the pressure sensor 6 are formed as a module structure made of micro-scale materials, and the module structure has a length, a width, and a height. The length, the width, and the height of the module structure are respectively between 1 mm and 999 mm, or between 1 μm and 999 μm, or between 1 nm and 999 nm, but embodiments are not limited thereto. In this embodiment, the module structure has a size in which the length of the module structure is between 1 μm and 999 μm, the width of the module structure is between 1 μm and 999 μm, and the height of the module structure is between 1 μm and 999 μm; alternatively, the module structure has a size in which the length of the module structure is between 1 nm and 999 nm, the width of the module structure is between 1 nm and 999 nm, and the height of the module structure is between 1 nm and 999 nm, but embodiments are not limited thereto.

The base 1 includes a valve loading area 11, an accommodation trough area 12, a gas inlet hole 13, an insertion hole 14, a first surface 15, and a second surface 16. The first surface 15 and the second surface 16 are opposite surfaces of the base 1. The valve loading area 11 is disposed on the first surface 15, and the accommodation trough area 12 is disposed on the second surface 16. The gas inlet hole 13 and the insertion hole 14 respectively penetrate the base 1 from the first surface 15 to the second surface 16, and the gas inlet hole 13 and the insertion hole 14 are respectively in communication with the accommodation trough area 12. The valve loading area 11 has a first recessed receiving chamber 11a, a plurality of first through holes 11b, a first protruding structure 11c, and a plurality of protruding posts 11d. The valve loading area 11 is recessed to form the first recessed receiving chamber 11a. The first protruding structure 11c extends from a center portion of the first recessed receiving chamber 11a. The first through holes 11b surround the first protruding structure 11c and penetrate the valve loading area 11 so as to be in communication with the accommodation trough area 12. The protruding posts 11d are respectively disposed at corners of the valve loading area 11. Moreover, an inner wall of the accommodation trough area 12 is recessed to form a gas collection chamber 12a, and the gas collection chamber 12a is in communication with the first through holes 11b.

Moreover, the valve loading area 11 may further include a second recessed receiving chamber 11e. The second recessed receiving chamber 11e and the first recessed receiving chamber 11a are spaced apart from each other. At least one second through hole 11f penetrates an inner wall of the second recessed receiving chamber 11e, and the second recessed receiving chamber 11e is in communication with the gas collection chamber 12a through the second through hole 11f. Accordingly, the number of the channels between the gas collection chamber 12a and the valve loading area 11 increases, thereby facilitating the gas transmission speed from the gas collection chamber 12a to the valve loading area 11.

Figure 4:
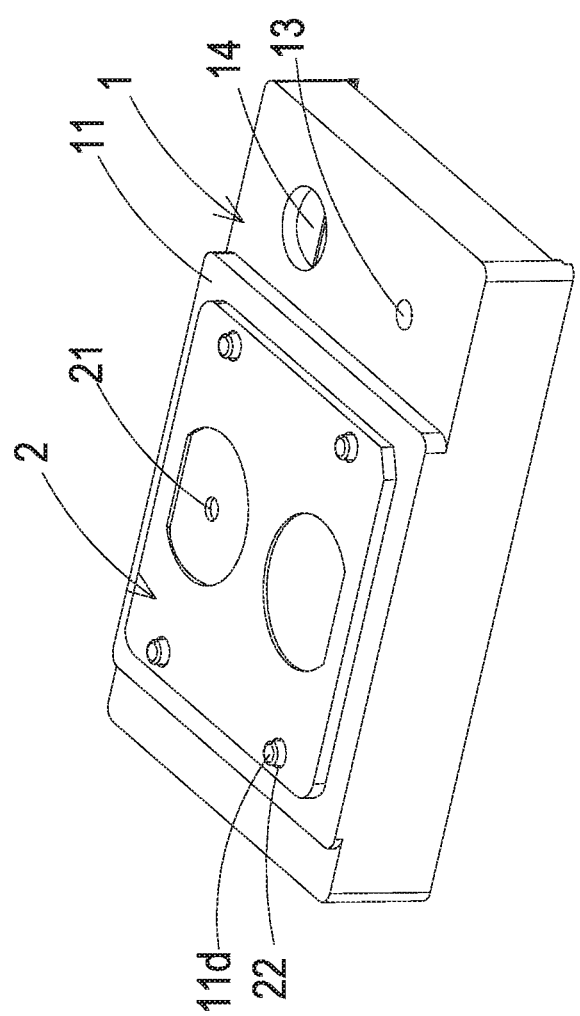
FIG. 4 illustrates a schematic perspective view showing that the valve plate is disposed on the base, according to the blood pressure measurement module of the exemplary embodiment.

Please refer to FIG. 2A and FIG. 4. The valve plate 2 is disposed on the valve loading area 11. The valve plate 2 has a valve hole 21 and a plurality of positioning perforations 22. The valve hole 21 and the first protruding structure 11c of the valve loading area 11 perpendicularly correspond to each other. The positioning perforations 22 respectively correspond to the protruding posts 11d, and the positioning perforations 22 are respectively inserted by the protruding posts 11d.

Figure 12:
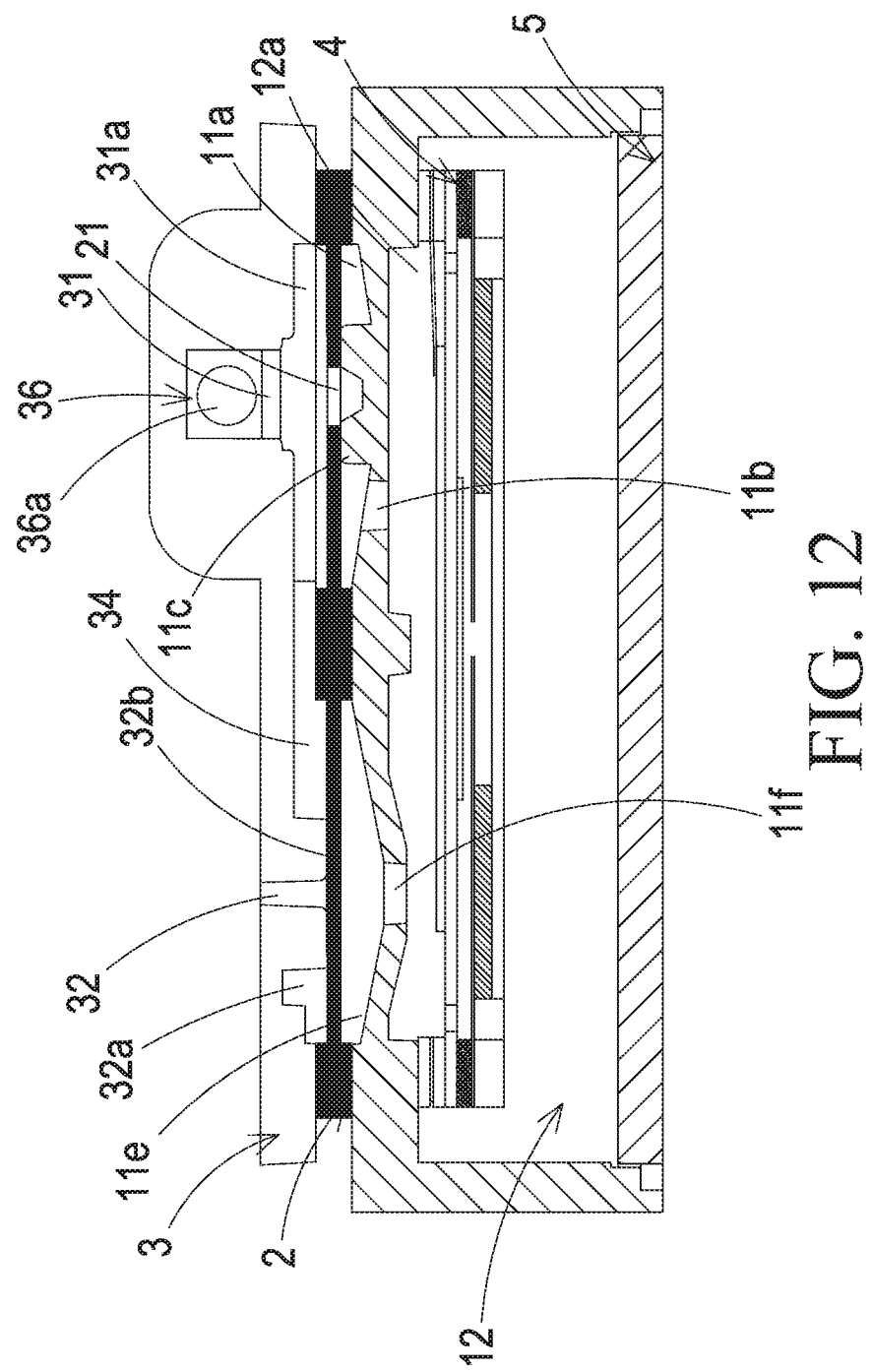
FIG. 12 illustrates a schematic cross-sectional view along line BB shown in FIG. 10.
Figure 17B:
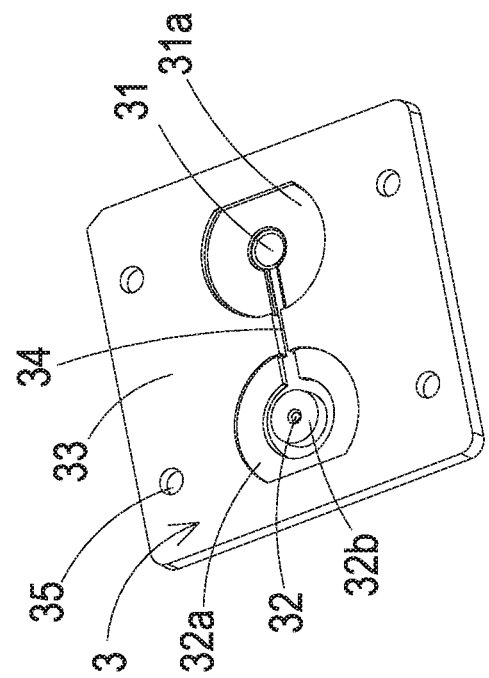
FIG. 17B illustrates a schematic perspective view of the top cover of the blood pressure measurement module of the another exemplary embodiment, from another perspective.
Figure 17A:
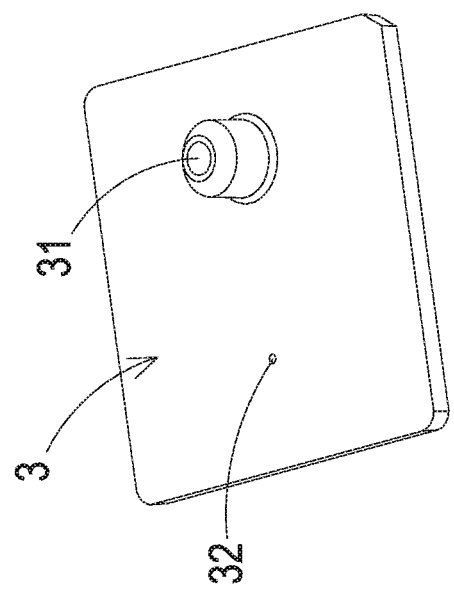
FIG. 17A illustrates a schematic perspective view of a top cover of the blood pressure measurement module of the another exemplary embodiment.

As shown in FIG. 17A and FIG. 17B, the top cover 3 has an inlet channel 31, a discharge hole 32, an assembling surface 33, a communication channel 34, and a plurality of positioning holes 35. The inlet channel 31 and the discharge hole 32 are spaced apart from each other. The assembling surface 33 covers the valve plate 2. A portion of the assembling surface 33 corresponding to a peripheral portion of the inlet channel 31 is recessed to form an inlet chamber 31a, and the inlet chamber 31a is in communication with the inlet channel 31. A portion of the assembling surface 33 corresponding to a peripheral portion of the discharge hole 32 is recessed to form a discharge chamber 32a, and the discharge chamber 32a is in communication with the discharge hole 32. The communication channel 34 is recessed from the assembling surface 33 and disposed between the inlet chamber 31a and the discharge chamber 32a, so that the inlet chamber 31a is in communication with the discharge chamber 32a. Moreover, a second protruding structure 32b extends from a periphery portion of the discharge chamber 32a and a periphery portion of the discharge hole 32. Please refer to FIG. 12. The valve plate 2 is loaded on the valve loading area 11 and is fixedly positioned between the base 1 and the top cover 3. At this time, the discharge hole 32 is opened at a center portion of the second protruding structure 32b, the second protruding structure 32b then abuts against the valve plate 2 to close the discharge hole 32, thereby normally forming a pre-force action.

Figure 11:
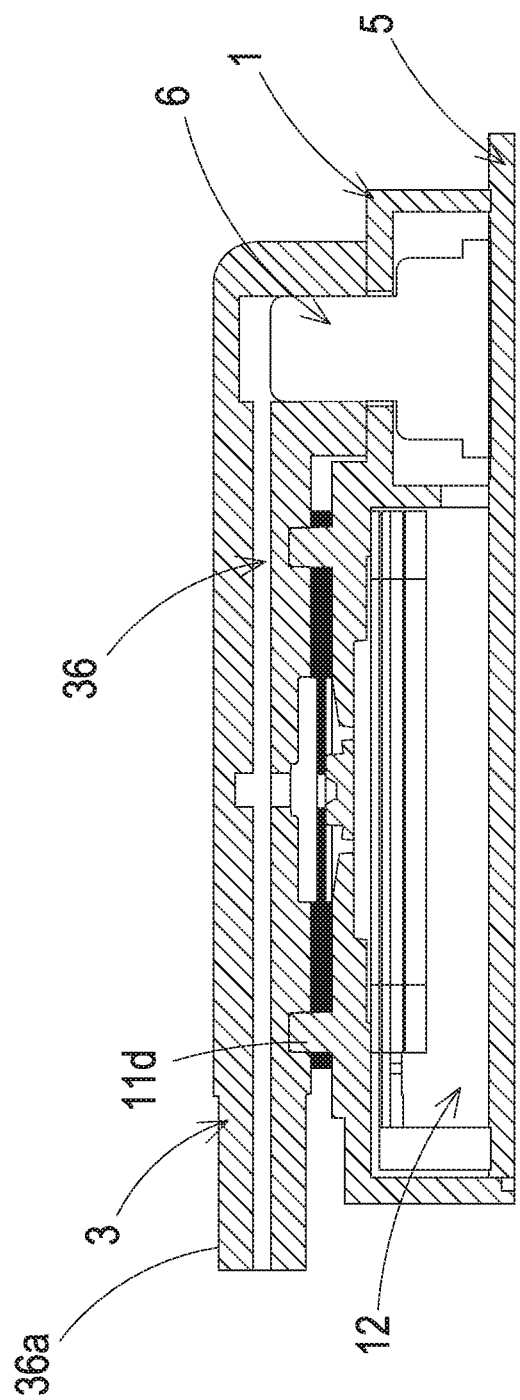
FIG. 11 illustrates a schematic cross-sectional view along line AA shown in FIG. 10.

Please refer to FIG. 2A, FIG. 2B, and FIG. 11. The positioning holes 35 are respectively disposed at four corners of the assembling surface 33 and respectively correspond to the protruding posts 11d of the valve loading area 11, and the positioning holes 35 are respectively inserted by the protruding posts 11d.

Figure 5:
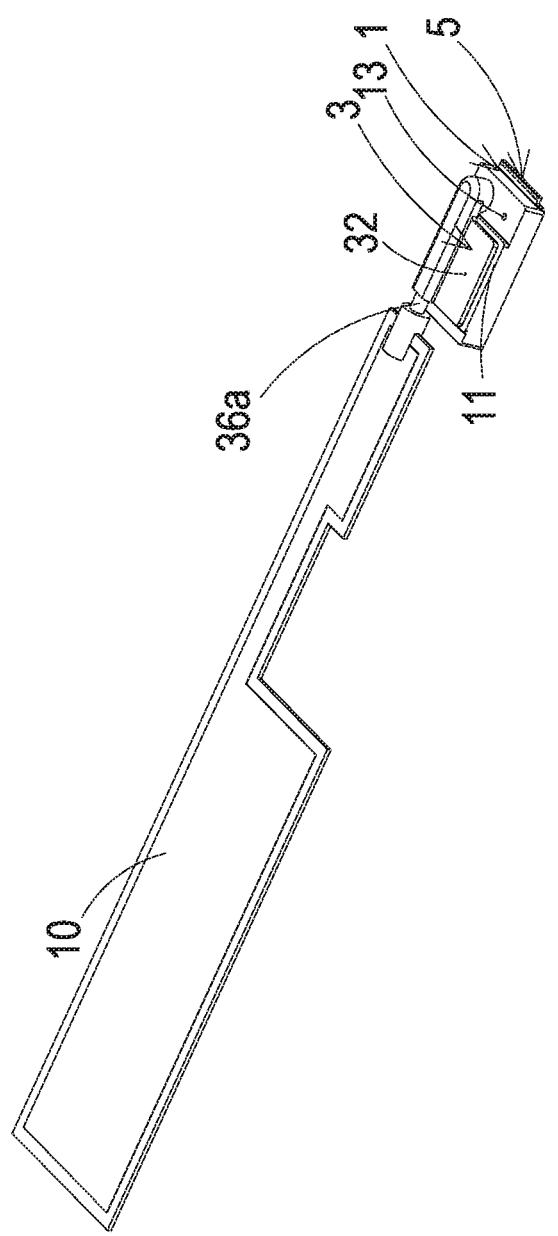
FIG. 5 illustrates a schematic perspective view showing that the blood pressure measurement module of the exemplary embodiment is connected to a gas bag.
Figure 10:
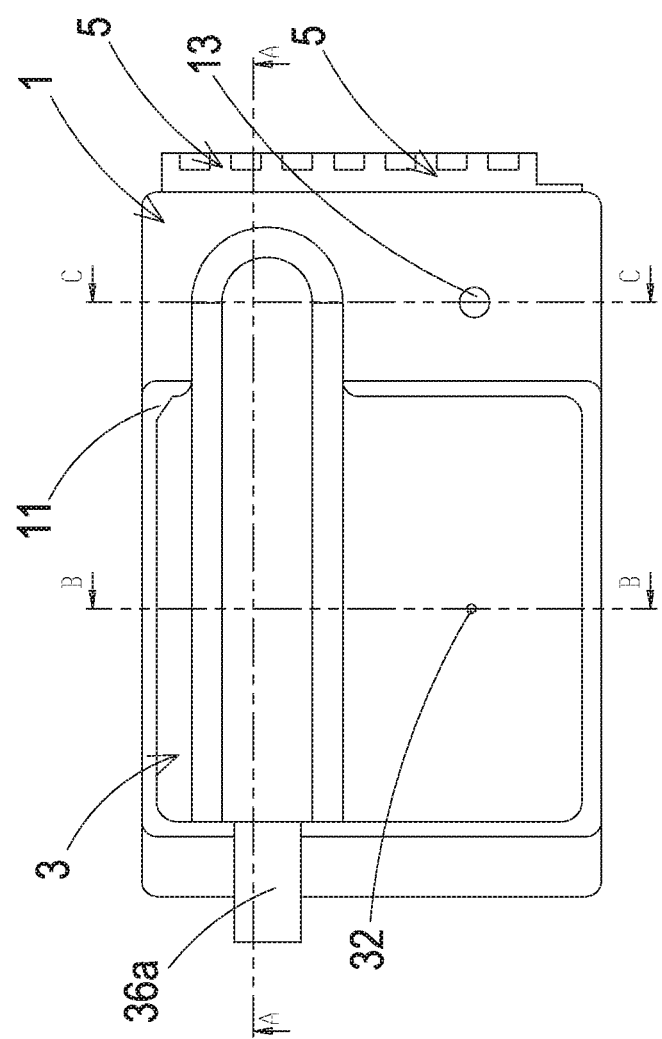
FIG. 10 illustrates a schematic top view of the blood pressure measurement module of the exemplary embodiment.
Figure 13:
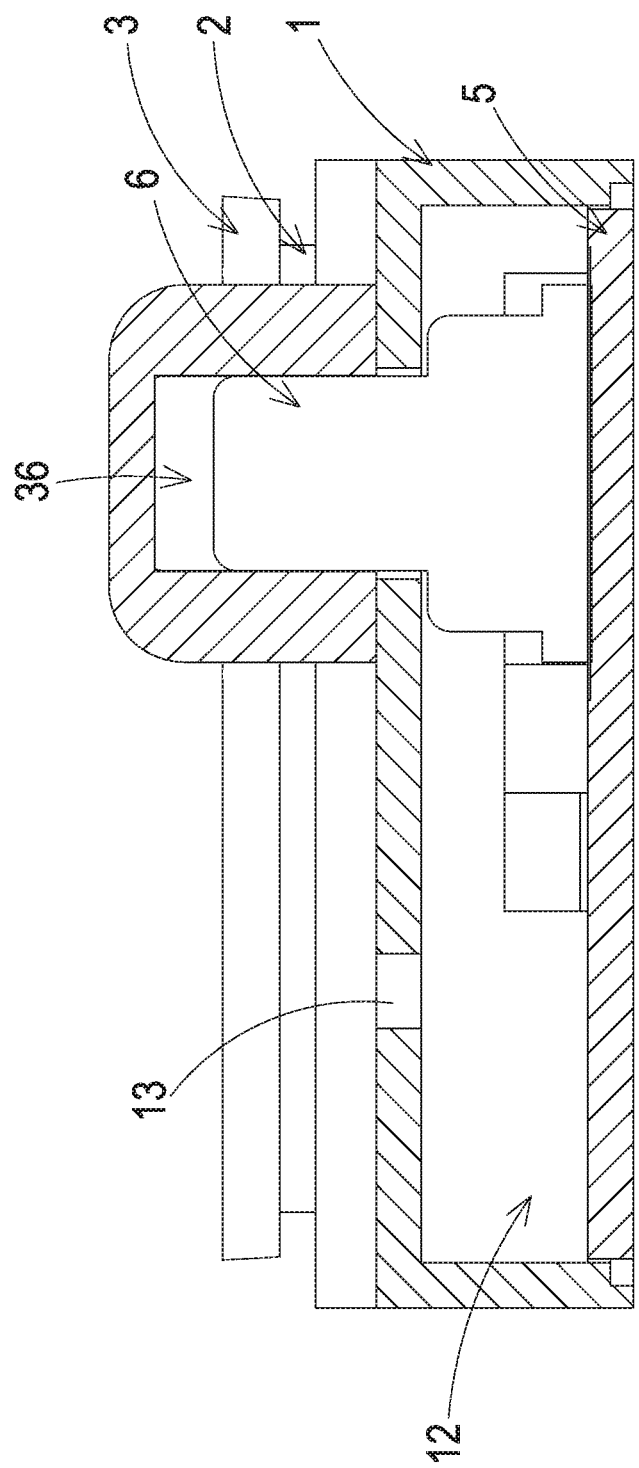
FIG. 13 illustrates a schematic cross-sectional view long line CC shown in FIG. 10.

Please refer to FIG. 2B and FIG. 5. The top cover 3 may further have a common channel 36. The common channel 36 is integrated with and in communication with the inlet channel 31. One of two ends of the common channel 36 extends to the pressure sensor 6 so as to cover the pressure sensor 6 (as shown in FIG. 13), the other end of the two ends of the common channel 36 is served as a connection end 36a (as shown in FIG. 10), and the connection end 36a is provided for connecting to a gas bag 10. Hence, the pressure sensor 6 is in communication with the gas bag 10 through the common channel 36 so as to perform gas pressure detection, thereby achieving blood pressure measurement. That is, the common channel 36 is a channel for gas communication among the pressure sensor 6, the micro pump 4 (through the inlet channel 31), and the gas bag 10.

Please refer to FIG. 2B. The micro pump 4 is disposed in the accommodation trough area 12, and the micro pump 4 covers the gas collection chamber 12a. The driving circuit board 5 covers the accommodation trough area 12, the driving circuit board 5 is electrically connected to the micro pump 4 so as to provide a driving signal for the micro pump 4, thereby controlling the operation of the micro pump 4. Moreover, the pressure sensor 6 is disposed on and electrically connected to the driving circuit board 5, and the pressure sensor 6 is in the insertion hole 14 of the base 1. One end of the pressure sensor 6 is inserted into the base 1, passes through the top cover 3, and is further connected to the gas bag 10 (as shown in FIG. 5).

Figure 6A:
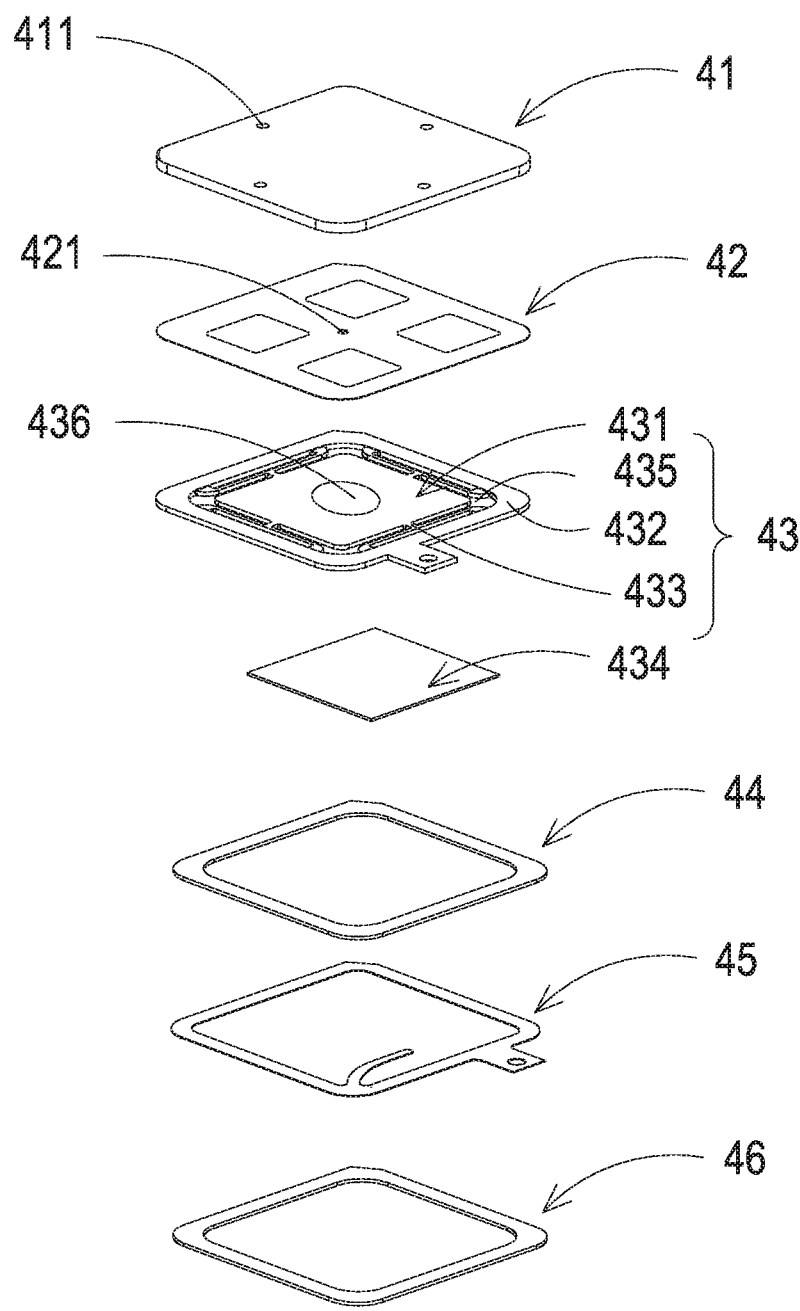
FIG. 6A illustrates a front exploded view of a micro pump of the blood pressure measurement module of the exemplary embodiment.
Figure 6B:
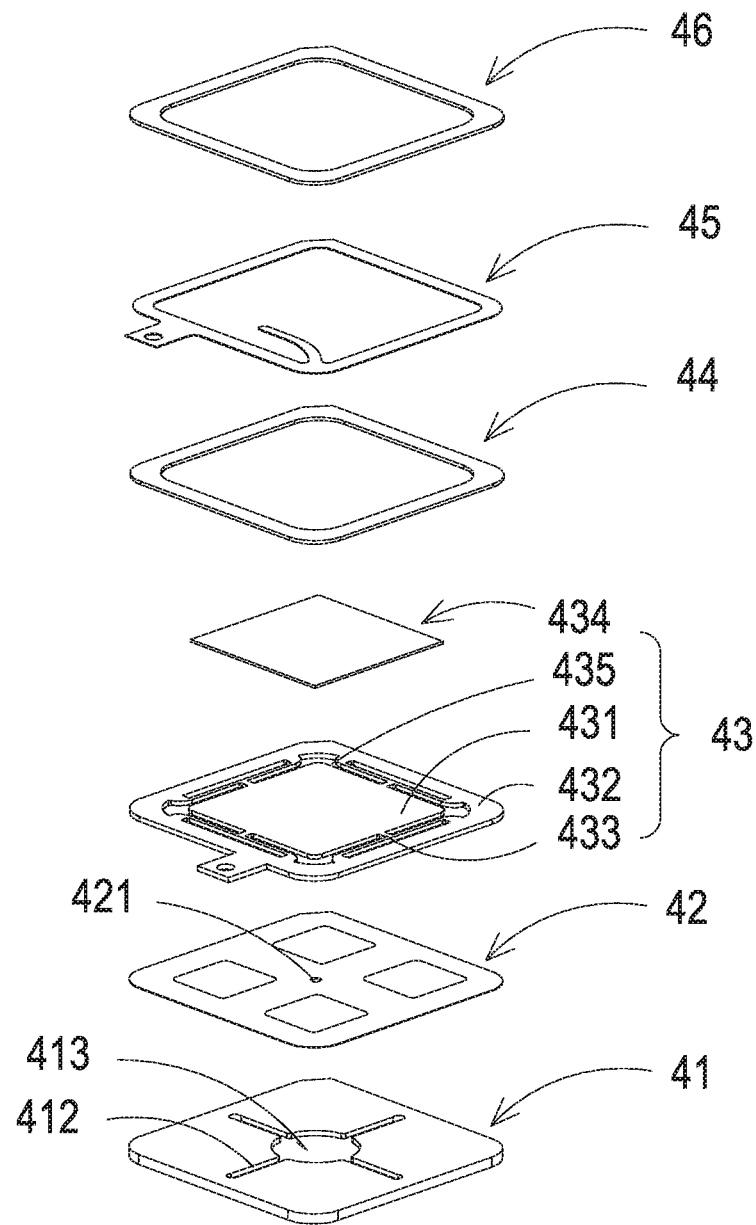
FIG. 6B illustrates a rear exploded view of the micro pump of the blood pressure measurement module of the exemplary embodiment.

Please refer to FIG. 6A and FIG. 6B. The micro pump includes an inlet plate 41, a resonance sheet 42, a piezoelectric actuator 43, a first insulation sheet 44, a conductive sheet 45, and a second insulation sheet 46. The piezoelectric actuator 43 is disposed correspondingly to the resonance sheet 42. The inlet plate 41, the resonance sheet 42, the piezoelectric actuator 43, the first insulation sheet 44, the conductive sheet 45, and the second insulation sheet 46 are sequentially stacked and assembled with each other.

The inlet plate 41 has at least one inlet hole 411, at least one convergence channel 412, and a convergence chamber 413. In this embodiment, the number of the inlet hole 411 is preferably four, but not limited thereto. The inlet plate 41 has a top surface and a bottom surface opposite to the top surface, and the inlet hole 411 penetrates the inlet plate 41 from the top surface to the bottom surface, so that the gas outside the micro pump 4 can flow into the micro pump 4 from the at least one inlet hole 411 due to the atmospheric pressure effect. The inlet plate 41 has at least one convergence channel 412, and the number of the convergence channel 412 corresponds to the number of the inlet hole 411 at another surface of the inlet plate 41. In this embodiment, the number of the inlet hole 411 is four, and correspondingly, the number of the convergence channel 412 is four as well. The convergence chamber 413 is at a center portion of the inlet plate 41. One of two ends of each of the four convergence channels 412 is in communication with the corresponding inlet hole 411, and the other end of the two ends of each of the four convergence channels 412 is in communication with the convergence chamber 413 at the center portion of the inlet plate 41. Accordingly, the gas flowing into the convergence channels 412 from the inlet holes 411 can be guided and converged at the convergence chamber 413. In this embodiment, the inlet plate 41 is a one-piece element integrally formed with the inlet holes 411, the convergence channels 412, and the convergence chamber 413.

In some embodiments, the inlet plate 41 may be made of stainless steel, but is not limited thereto. In some other embodiments, the depth of the convergence chamber 413 is substantially equal to the depth of the convergence channel 412, but is not limited thereto.

The resonance sheet 42 is made of a flexible material, but is not limited thereto. Moreover, the resonance sheet 42 has a perforation 421 corresponding to the convergence chamber 413 of the inlet plate 41, whereby the gas in the convergence chamber 413 can pass through the resonance sheet 42. In some other embodiments, the resonance sheet 42 is made of copper, but is not limited thereto.

The piezoelectric actuator 43 is assembled by a suspension plate 431, an outer frame 432, at least one supporting element 433, and a piezoelectric element 434. The suspension plate 431 has a square shape, and the suspension plate 431 is capable of bending and vibrating. The outer frame 432 is disposed around the periphery of the suspension plate 431. The at least one supporting element 433 connected between the suspension plate 431 and the outer frame 432 to provide a flexible support for the suspension plate 431. The piezoelectric element 434 also has a square shape and is attached to one surface of the suspension plate 431 so as to drive the suspension plate 431 to bend and vibrate when the piezoelectric element 434 is applied with a voltage. The side length of the piezoelectric element 434 is smaller than or equal to a side length of the suspension plate 431. A plurality of gaps 435 is formed among the suspension plate 431, the outer frame 432, and the supporting element 433 for the gas passing therethrough. Moreover, the piezoelectric actuator 43 further includes a protruding portion 436 disposed on the other surface of the suspension plate 431. That is, the piezoelectric element 434 and the protruding portion 436 are respectively disposed on the two opposite surfaces of the suspension plate 431.

Figure 7A:
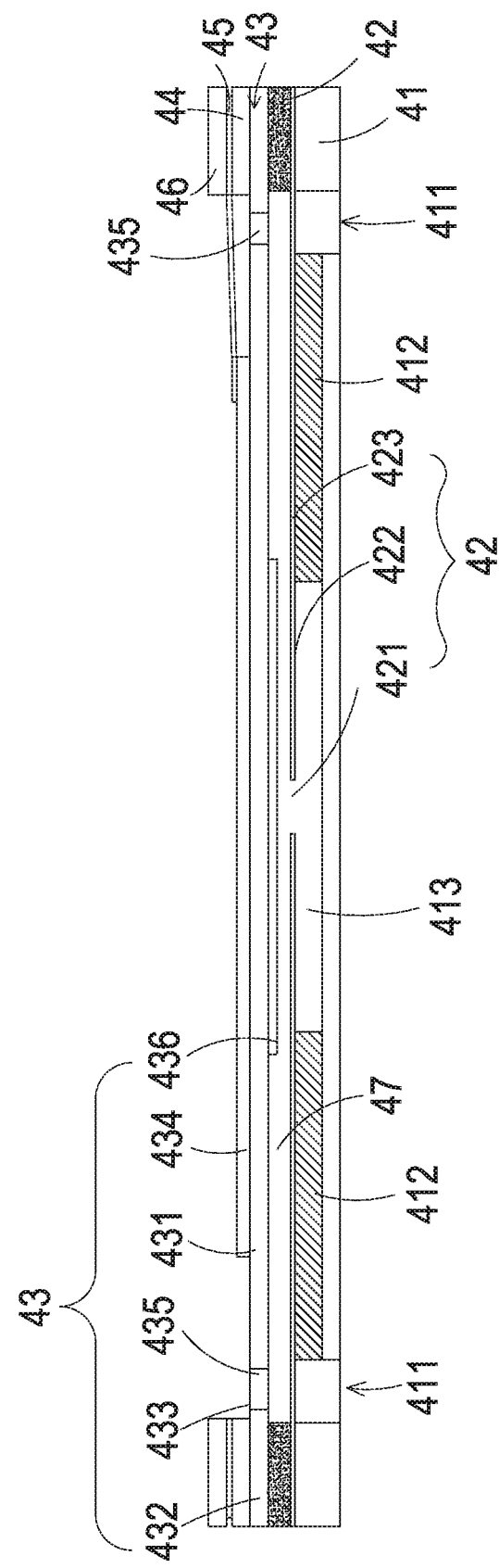
FIG. 7A illustrates a schematic cross-sectional view of the micro pump of the blood pressure measurement module of the exemplary embodiment.

As shown in FIG. 7A, the inlet plate 41, the resonance sheet 42, the piezoelectric actuator 43, the first insulation sheet 44, the conductive sheet 45, and the second insulation sheet 46 are arranged sequentially and stacked with each other. The thickness of the suspension plate 431 of the piezoelectric actuator 43 is smaller than the thickness of the outer frame 432. Thus, when the resonance sheet 42 is stacked on the piezoelectric actuator 43, a chamber space 47 can be formed among the suspension plate 431, the outer frame 432, and the resonance sheet 42.

Figure 7B:
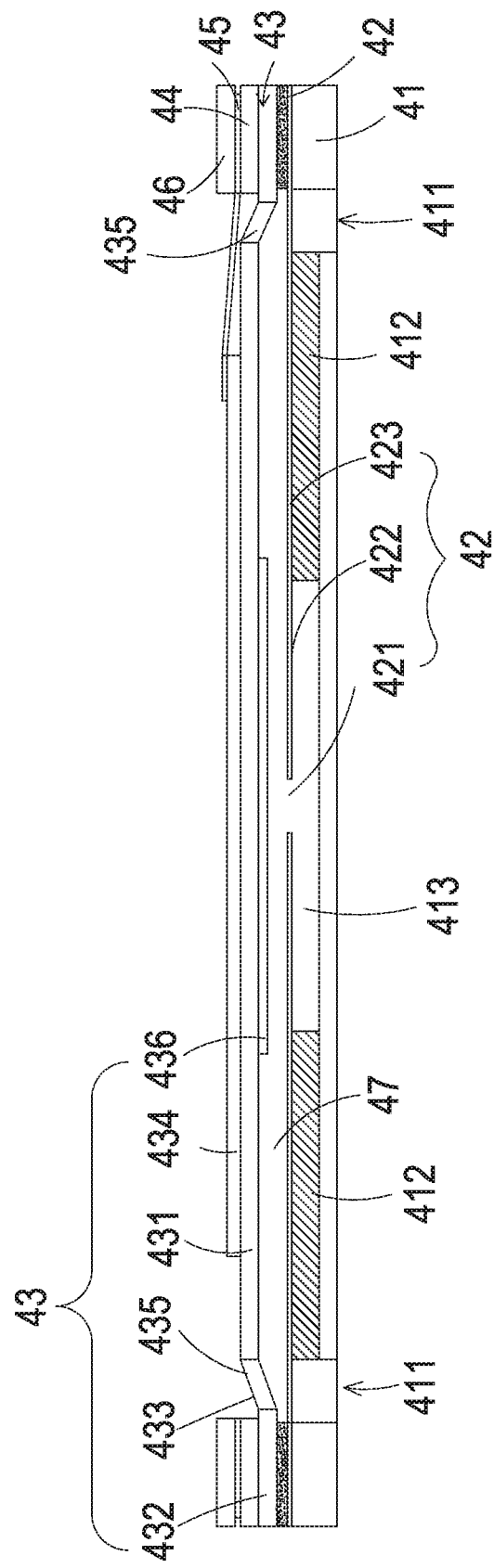
FIG. 7B illustrates a schematic cross-sectional view of a blood pressure measurement module according to another embodiment of the present disclosure.

Please refer to FIG. 6B. FIG. 6B shows another embodiment of the micro pump 4. Most of the elements in FIG. 7B are similar to the corresponding elements in FIG. 6A, which are not repeated here. The difference between the embodiment shown in FIG. 7B and the embodiment shown in FIG. 6A is that, when the micro pump 4 in FIG. 7B does not operate, the suspension plate 431 of the piezoelectric actuator 43 extends away from the resonance sheet 42 by a stamping process, so that the suspension plate 431 and the outer frame 432 are not aligned at the same level. The extended distance of the suspension plate 431 may be adjusted by the supporting elements 433. In such embodiments, the supporting elements 433 are not parallel to the suspension plate 431, so that part of the piezoelectric actuator 43 has a convex profile.

Figure 7C:
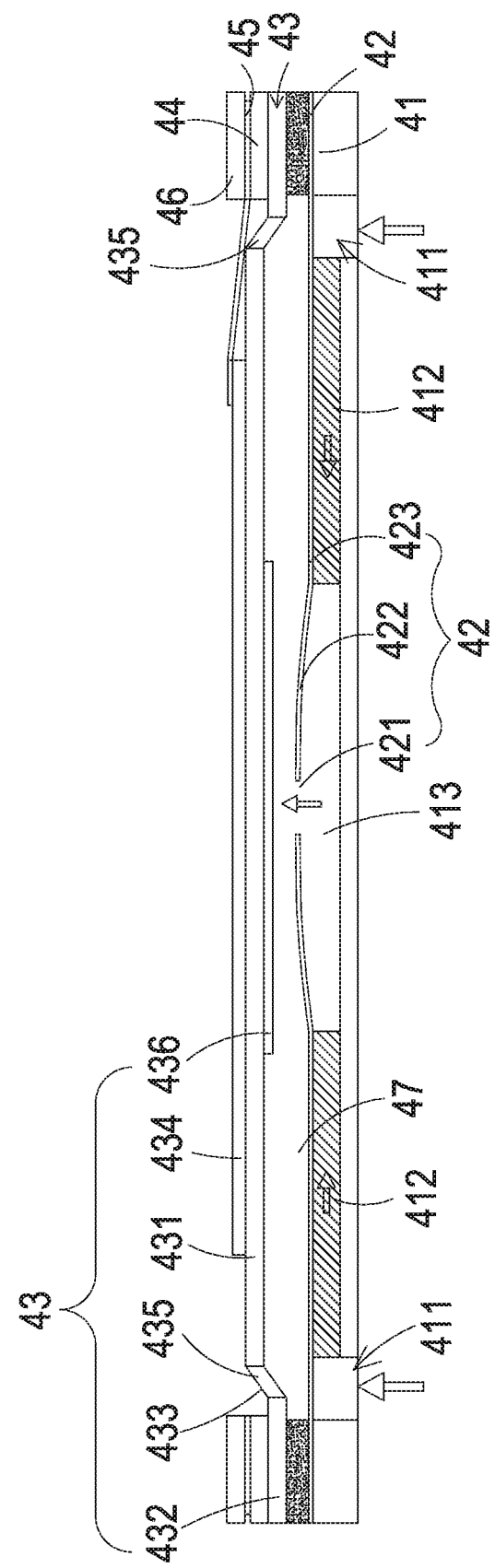
FIG. 7C to FIG. 7E illustrate schematic cross-sectional views showing the micro pump according to the exemplary embodiment of the present disclosure at different operation steps.
Figure 7D:
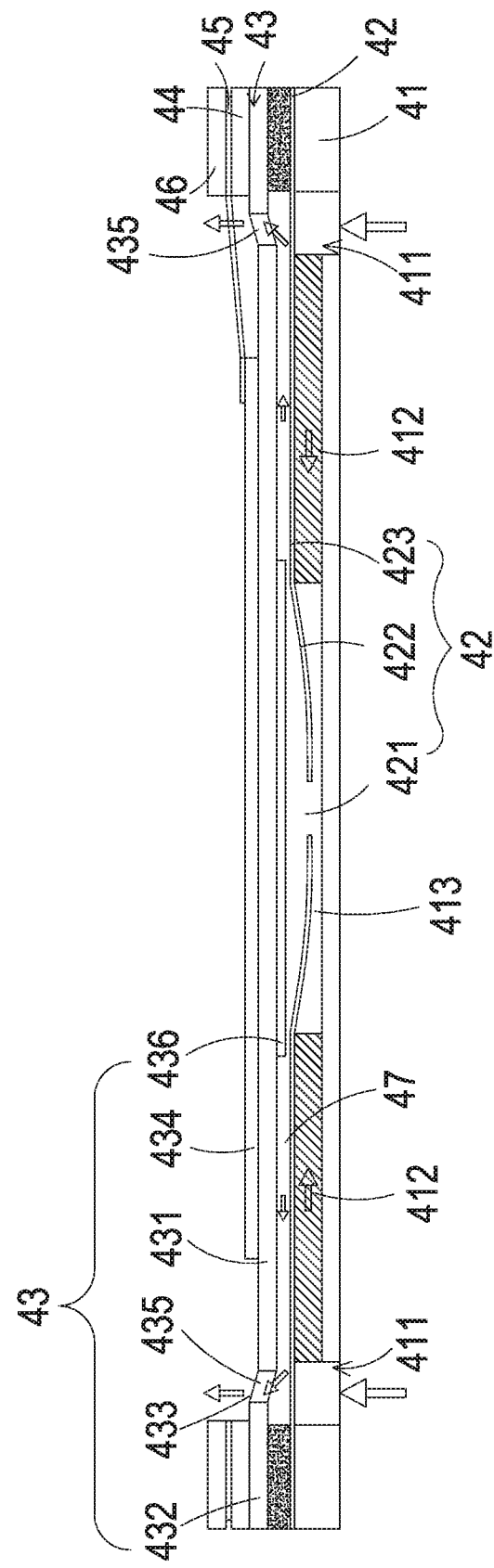
Figure 7E:
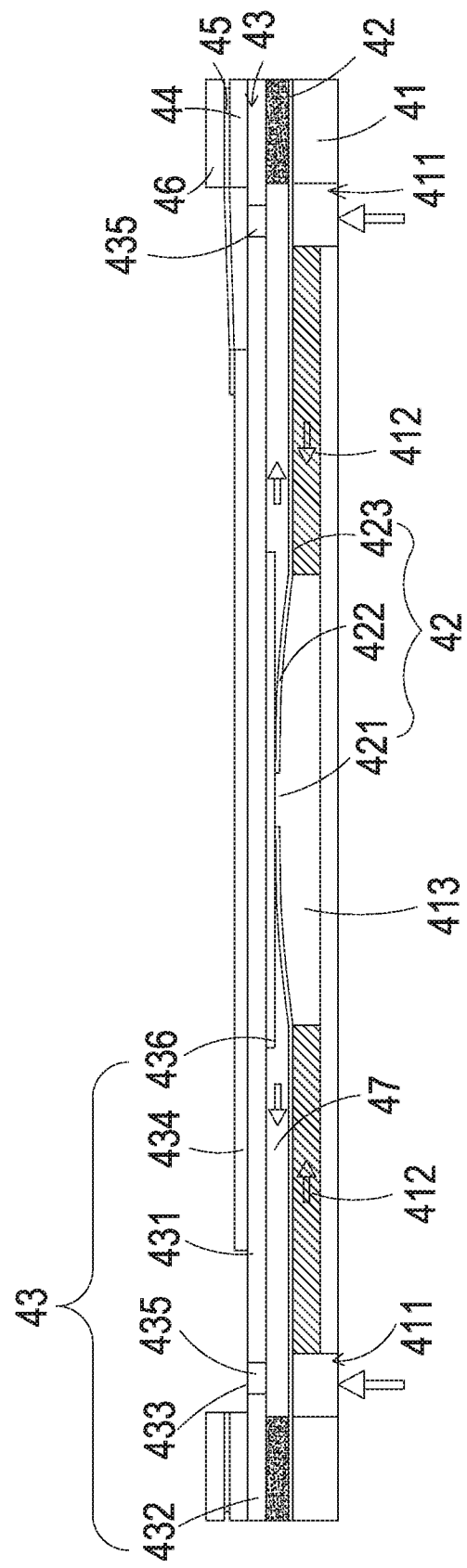

In order to understand the operation steps of the aforementioned micro pump 4 in transmitting gas, please refer to FIG. 7C to FIG. 7E. Please refer to FIG. 7C first, the piezoelectric element 434 of the piezoelectric actuator 43 deforms after being applied with a driving voltage, and the piezoelectric element 434 drives the suspension plate 431 to move away from the inlet plate 41. Thus, the volume of the chamber space 47 is increased and a negative pressure is generated inside the chamber space 47, thereby drawing the gas in the convergence chamber 413 into the chamber space 47. At the same time, owing to the resonance effect, the resonance sheet 42 is bent away from the inlet plate 41 correspondingly, which also increases the volume of the convergence chamber 413. Furthermore, since the gas inside the convergence chamber 413 is drawn into the chamber space 47, the convergence chamber 213 is in a negative pressure state as well. Therefore, the gas can be drawn into the convergence chamber 413 through the inlet hole 411 and the convergence channel 412. Then, please refer to FIG. 7D. The piezoelectric element 234 drives the suspension plate 431 to move toward the inlet plate 41, thereby compressing the chamber space 47. Similarly, since the resonance sheet 42 resonates with the suspension plate 431, the resonance sheet 42 also moves toward the inlet plate 41, thereby pushing the gas in the chamber space 47 to be transmitted out of the micro pump 4 through the at least one gap 435.

Last, please refer to FIG. 6E. When the suspension plate 431 moves resiliently to its original position, the resonance sheet 42 still moves away from the inlet plate 41 due to its inertia momentum. At the time, the resonance sheet 42 compresses the chamber space 47, so that the gas in the chamber space 47 is moved toward the gap 435 and the volume of the convergence chamber 413 is increased. Accordingly, the gas can be drawn into the convergence chamber 413 continuously through the inlet holes 411 and the convergence channels 412 and can be converged at the convergence chamber 413. By continuously repeating the operation steps of the micro pump 4 shown in FIG. 7C to FIG. 7E, the micro pump 4 can make the gas continuously enter into the flow paths formed by the inlet plate 41 and the resonance sheet 42 from the inlet holes 411, thereby generating a pressure gradient. The gas is then transmitted outward through the gap 435. As a result, the gas can flow at a relatively high speed, thereby achieving the effect of gas transmission of the micro pump 4.

Figure 8A:
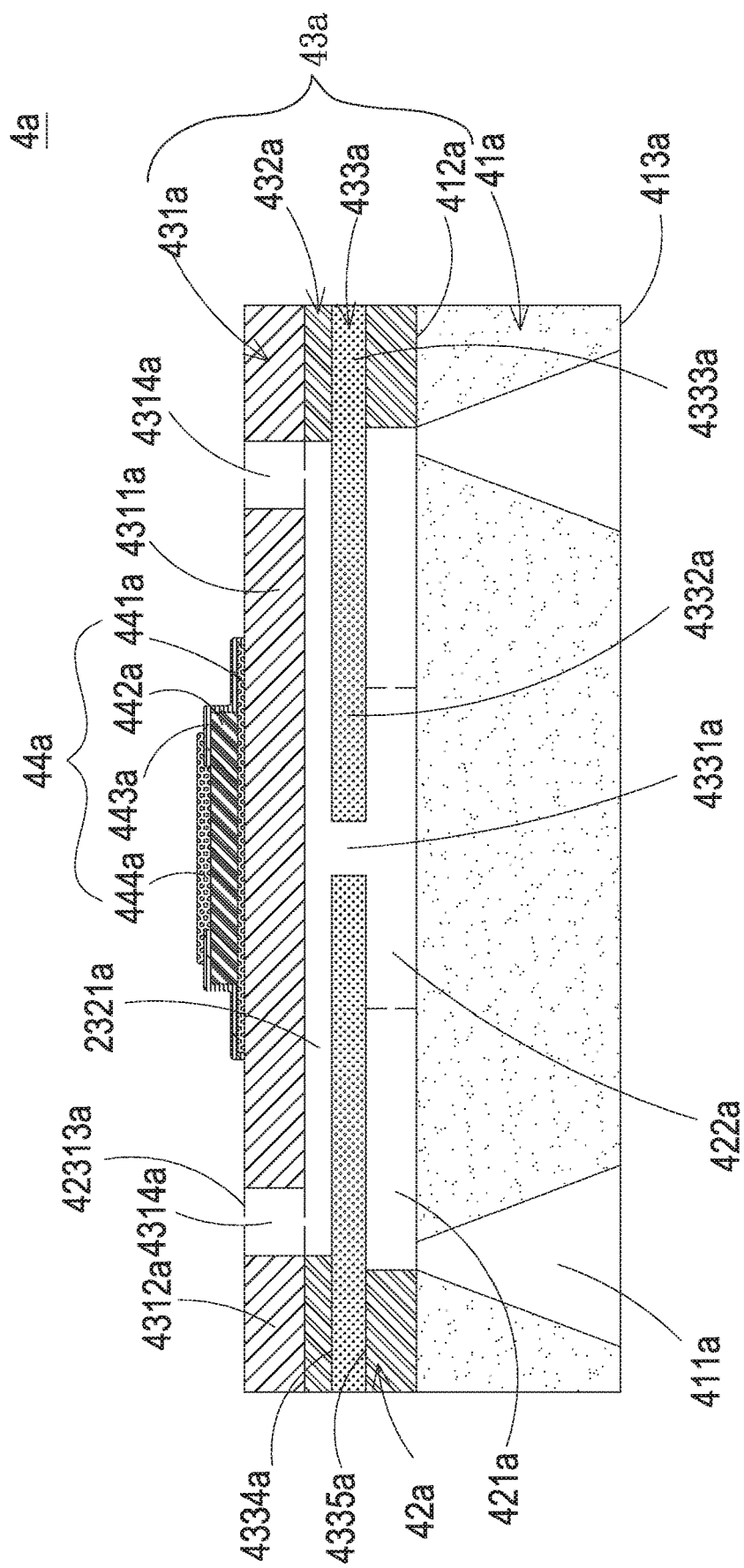
FIG. 8A illustrates a schematic cross-sectional view of a microelectromechanical systems (MEMS) pump of the blood pressure measurement module of the exemplary embodiment.
Figure 8B:
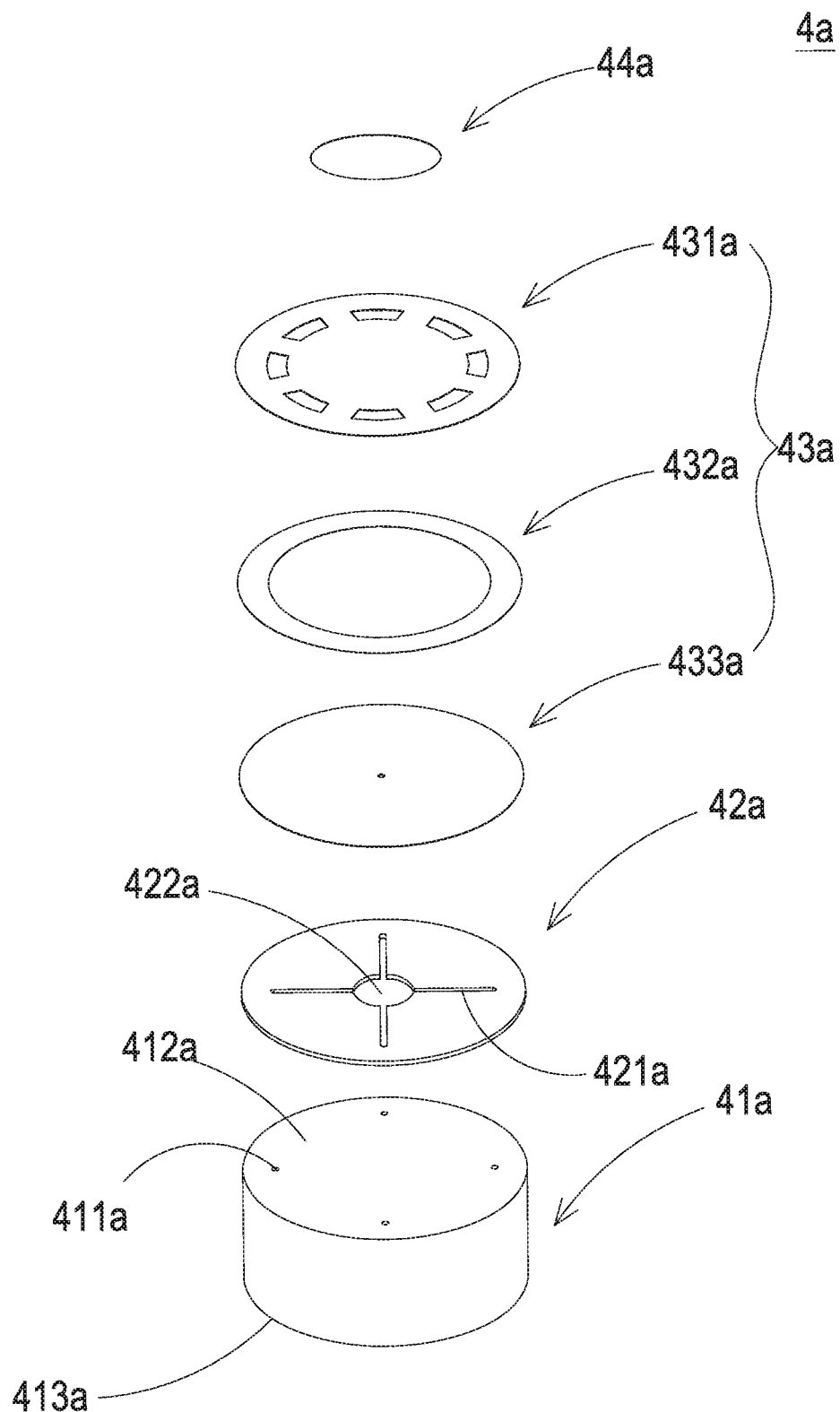
FIG. 8B illustrates a schematic exploded view of the MEMS pump of the blood pressure measurement module of the exemplary embodiment.

In another embodiment, the micro pump 4 may be a microelectromechanical systems (MEMS) pump 4a. Please refer to FIG. 8A and FIG. 8B. The MEMS pump 4a includes a first substrate 41a, a first oxide layer 42a, a second substrate 43a, and a piezoelectric component 44a. It should be understood that in FIG. 8B, components of the MEMS pump 4a cannot be actually taken apart since the MEMS pump 4a is fabricated by semiconductor manufacturing processes including epitaxy, deposition, lithography, and etching. However, in order to clearly explain the detailed structure of the MEMS pump 4a, the exploded view is illustrated in FIG. 8B and used to explain the characteristics of the MEMS pump 4a.

The first substrate 41a is a silicon wafer (Si wafer), and the thickness of the Si wafer may be between 150 and 400 µm. The first substrate 41a has a plurality of ventilation holes 411a, a substrate first surface 412a, and a substrate second surface 413a. In this embodiment, the number of the ventilation holes 411a is four, but not limited thereto. Each of the ventilation holes 411a penetrates the first substrate 41a from the substrate second surface 413a to the substrate first surface 412a. In order to improve the inflow efficiency of the ventilation holes 411a, each of the ventilation holes 411a is a conical hole, that is, each of the ventilation holes 411a is conical and tapered from the substrate second surface 413a to the substrate first surface 412a.

The first oxide layer 42a is a silicon dioxide ($SiO_2$) film. The thickness of the $SiO_2$ film is between 10 and 20 µm. The first oxide layer 42a is stacked on the substrate first surface 412a of the first substrate 41a. The first oxide layer 42a has a plurality of convergence troughs 421a and a convergence chamber 422a. The number and the position of the convergence trough 421a correspond to the number and the position of the ventilation holes 411a in the first substrate 41a. In this embodiment, the number of the convergence troughs 421a is four as well. One of two ends of each of the four convergence troughs 421a is in communication with the corresponding ventilation hole 411a in the first substrate 41a. The other end of the two ends of each of the four convergence troughs 421a is in communication with the convergence chamber 422a. Thus, after a gas enters into the first substrate 41a from the ventilation holes 411a, the gas flows through the convergence troughs 421a and then is converged at the convergence chamber 422a.

The second substrate 43a is a silicon-on-insulator (SOI) wafer, and the second substrate 43a includes a silicon wafer layer 431a, a second oxide layer 432a, and a silicon material layer 433a. The thickness of the silicon wafer layer 431a is between 10 and 20 µm. The silicon wafer layer 431a has an actuation portion 4311a, an outer peripheral portion 4312a, a plurality of connection portions 4313a, and a plurality of fluid channels 4314a. The actuation portion 4311a is circular. The outer peripheral portion 4312a has a hollow ring shape and surrounds the periphery of the actuation portion 4311a. The connection portions 4313a are respectively located between and connected between the actuation portion 4311a and the outer peripheral portion 4312a for providing flexible support function. The fluid channels 4314a surround the periphery of the actuation portion 4311a and are located between the connection portions 4313a.

The second oxide layer 432a is made of silicon oxide. The thickness of the second oxide layer 432a is between 0.5 and 2 µm. The second oxide layer 432a is formed on the silicon wafer layer 431a. The second oxide layer 432a has a hollow ring shape, and the second oxide layer 432a and the silicon wafer layer 431a together define a vibration chamber 4321a. The silicon material layer 433a has a circular shape and stacked on the second oxide layer 432a. The silicon material layer 433a is combined with the first oxide layer 42a. The silicon material layer 433a is a silicon dioxide ($SiO_2$) film, and the thickness of the silicon material layer 433a may be between 2 and 5 µm. The silicon material layer 433a has a third through hole 4331a, a vibration portion 4332a, a fixed portion 4333a, a third surface 4334a, and a fourth surface 4335a. The third through hole 4331a is located at a center portion of the silicon material layer 433a. The vibration portion 4332a is located at a peripheral area of the third through hole 2331a, and the vibration portion 4332a is perpendicularly corresponding to the vibration chamber 4321a. The fixed portion 4333a is located at a peripheral area of the silicon material layer 433a, and the vibration portion 44332a is fixed to the second oxide layer 432a by the fixed portion 4333a. The third surface 4334a is assembled with the second oxide layer 432a, and the fourth surface 4335a is assembled with the first oxide layer 42a. The piezoelectric component 44a is stacked on the actuation portion 4311a of the silicon wafer layer 431a.

The piezoelectric component 44a has a circular shape and includes a lower electrode layer 441a, a piezoelectric layer 442a, an insulation layer 443a, and an upper electrode layer 444a. The lower electrode layer 441a may be stacked on the actuation portion 4311a of the silicon wafer layer 431a, and the piezoelectric layer 442a may be stacked on the lower electrode layer 441a. The piezoelectric layer 442a and the lower electrode layer 441a are electrically connected through the contacted area between each other. Moreover, the width of the piezoelectric layer 442a may be smaller than the width of the lower electrode layer 441a, and thus the lower electrode layer 441a is not completely covered by the piezoelectric layer 442a. The insulation layer 443a is stacked on part of the piezoelectric layer 442a and the remaining portion of the surface of the lower electrode layer 441a which is not covered by the piezoelectric layer 442a. Then, the upper electrode layer 444a is stacked on the insulation layer 443a and the remaining portion of the surface of the piezoelectric layer 442a which is not covered by the insulation layer 443a, and thus the upper electrode layer 444a is electrically connected to the piezoelectric layer 442a through the contact between each other. Moreover, since the insulation layer 443a is inserted between the upper electrode layer 444a and the lower electrode layer 441a, a short circuit condition caused by the direct contact between the upper electrode layer 444a and the lower electrode layer 441a could be avoided.

Figure 9A:
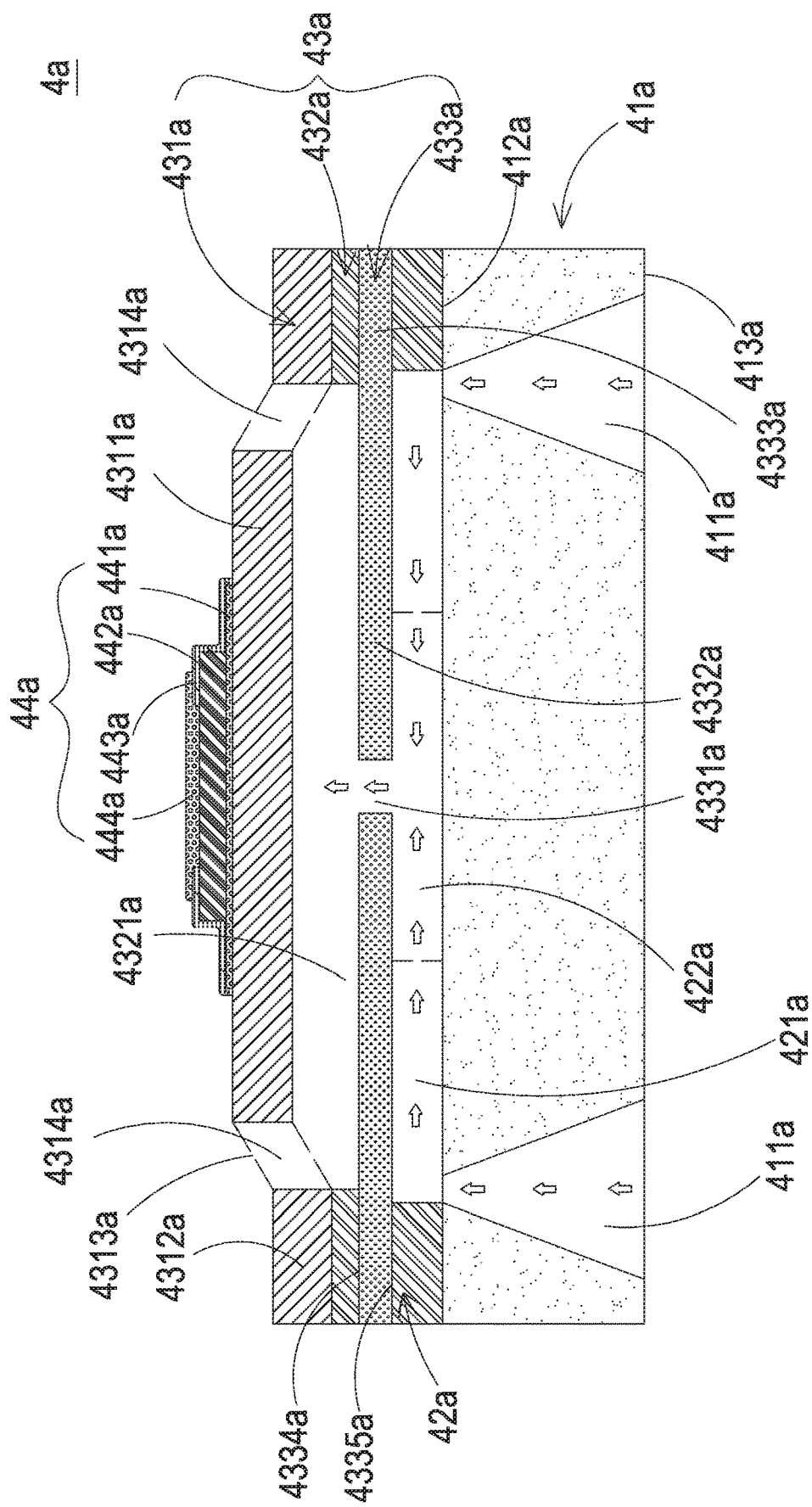
FIG. 9A to FIG. 9C illustrate schematic cross-sectional views showing the MEMS pump according to the exemplary embodiment of the present disclosure at different operation steps.
Figure 9B:
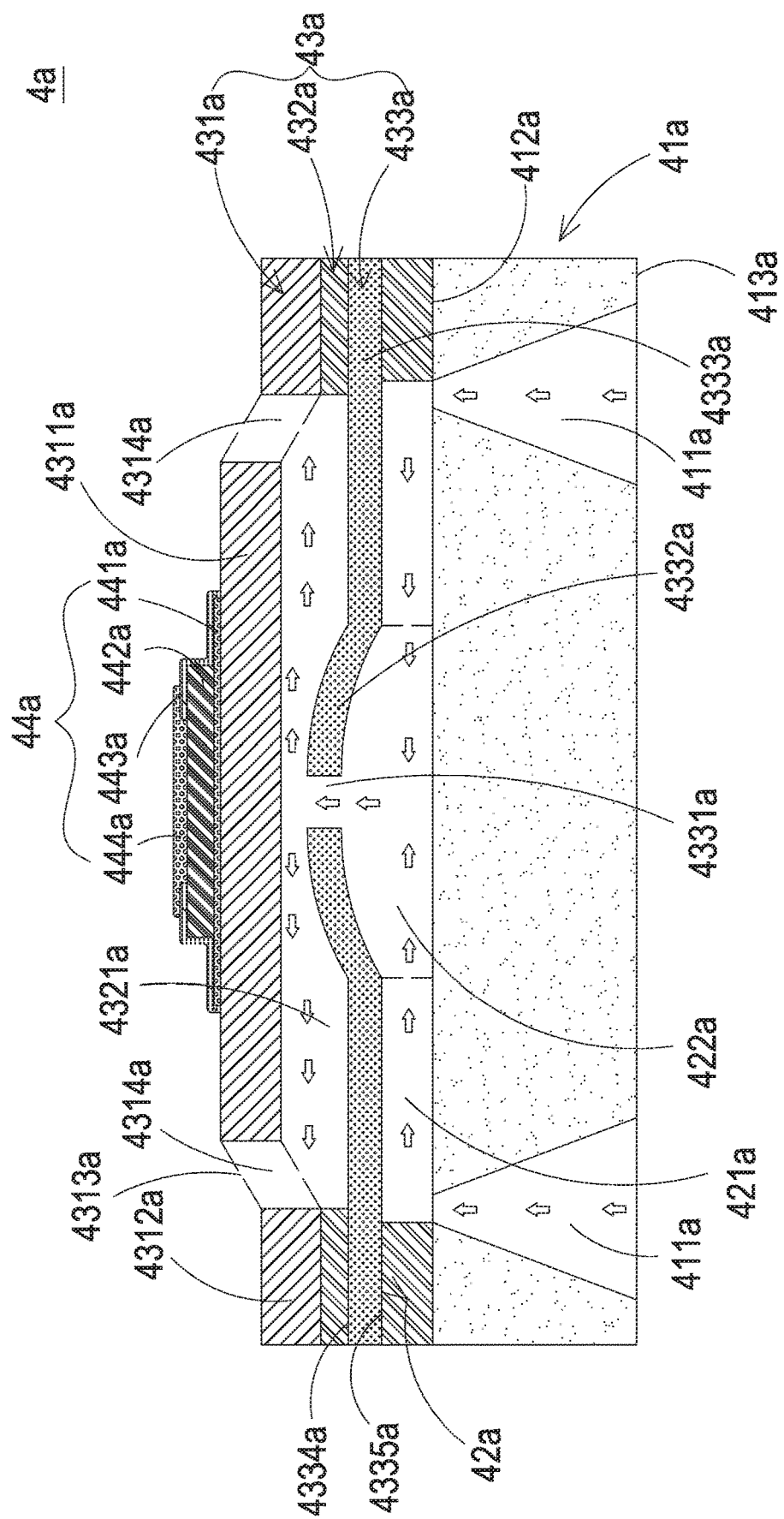
Figure 9C:
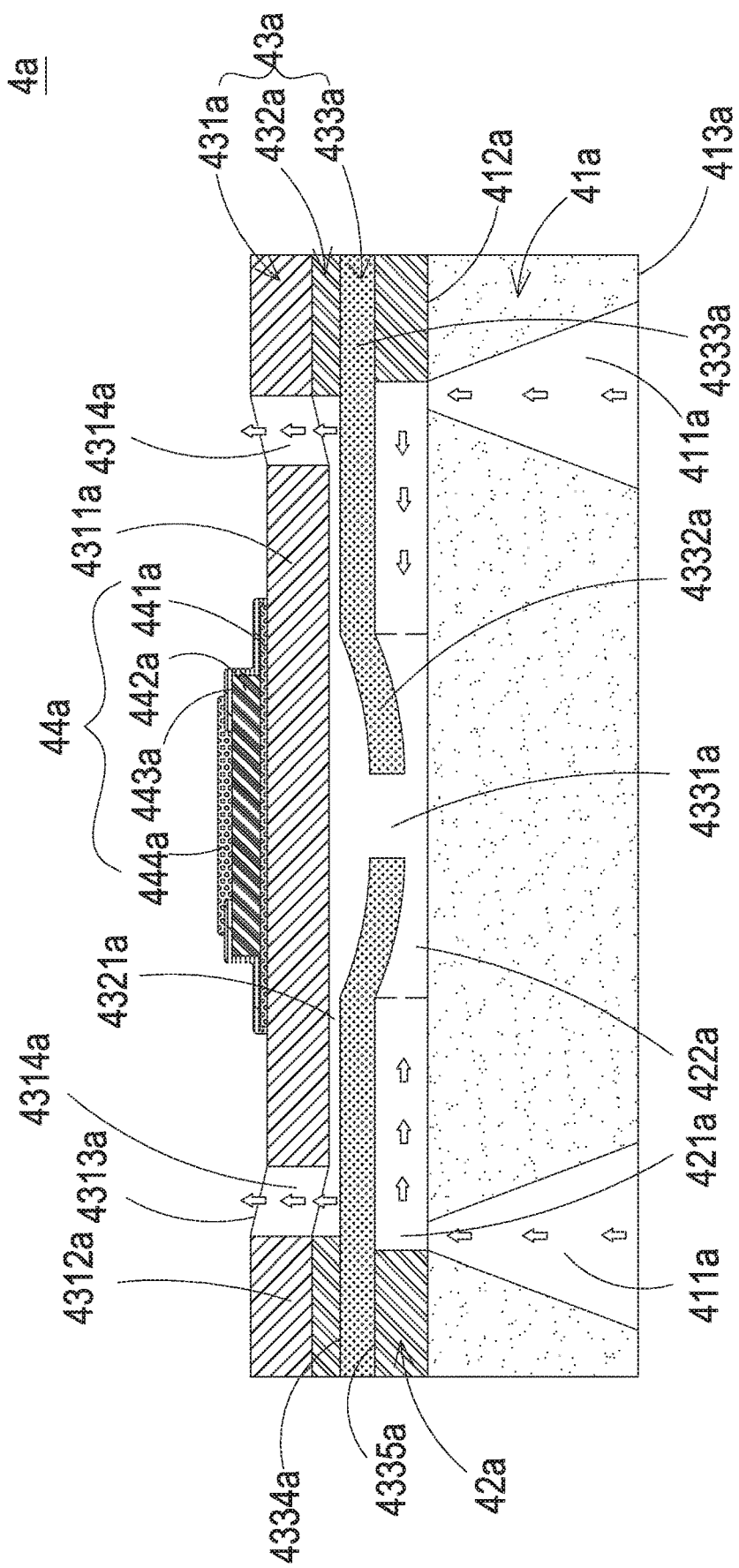

Please refer to FIG. 9A to FIG. 9C. FIG. 9A to FIG. 9C illustrate schematic cross-sectional views showing the micro-electromechanical systems pump 4a of the present disclosure at different operation steps. Please refer to FIG. 9A first, when the lower electrode layer 441a and the upper electrode layer 444a of the piezoelectric component 44a receive a driving voltage and a driving signal (not shown in the figure), the voltage and the signal are transmitted to the piezoelectric layer 442a. After the piezoelectric layer 442a is applied with the driving voltage and the driving signal, the piezoelectric layer 442a starts to deform because of the reverse piezoelectric effect, thereby driving the actuation portion 4311a of the silicon wafer layer 431a to move correspondingly. When the actuation portion 4311a is driven upwardly by the piezoelectric component 44a and thus the distance between the actuation portion 4311a and the second oxide layer 432a increases, the volume of the vibration chamber 4321a in the second oxide layer 432a increases as well. Hence, the pressure in the vibration chamber 4321a becomes negative, and thus the gas in the convergence chamber 422a of the first oxide layer 42a is drawn into the vibration chamber 4321a through the third through hole 4331a. Please refer to FIG. 9B, when the actuation portion 4311a is driven upwardly by the piezoelectric component 44a, the vibration portion 4332a of the silicon material layer 433a is moved upwardly due to the resonance effect. When the vibration portion 4332a is moved upwardly, the space of the vibration chamber 4321a is compressed and the gas in the vibration chamber 4321a is pushed to fluid channels 4314a of the silicon wafer layer 431a, so that the gas can be discharged upwardly through the fluid channels 4314a. When the vibration portion 4332a is moved upwardly to compress the space of the vibration chamber 4321a, the volume of the convergence chamber 422a increases owing to the movement of the vibration portion 4332a. Hence, the pressure in the convergence chamber 422a becomes negative, and thus the gas outside of the MEMS pump 4a is drawn into the convergence chamber 422a through the ventilation holes 411a. In the last step, as shown in FIG. 9C, when the actuation portion 4311a of the silicon wafer layer 431a is driven downwardly by the piezoelectric component 44a, the gas in the vibration chamber 4321a is pushed to the fluid channels 4314a and then discharged out. The vibration portion 4332a of the silicon material layer 433a is also driven by the actuation portion 4311a and thus moved downwardly; at the same time, the vibration portion 4332a compresses the gas in convergence chamber 422a and forces the gas to move to the vibration chamber 4321a through the third through hole 4331a. Accordingly, when the actuation portion 4311a is driven upwardly by the piezoelectric component 44a again later, the volume of the vibration chamber 4321a greatly increases, thereby generating a larger suction force to draw the gas into the vibration chamber 4321a. By repeating the aforementioned steps, the actuation portion 4311a can be continually driven by the piezoelectric component 44a to move upwardly and downwardly, and the vibration portion 4332a is also driven to move upwardly and downwardly correspondingly. Thus, the internal pressure of the MEMS pump 4a can be changed periodically so as to draw and discharge the gas continually, thereby completing the pumping process of the MEMS pump 4a.

Figure 14A:
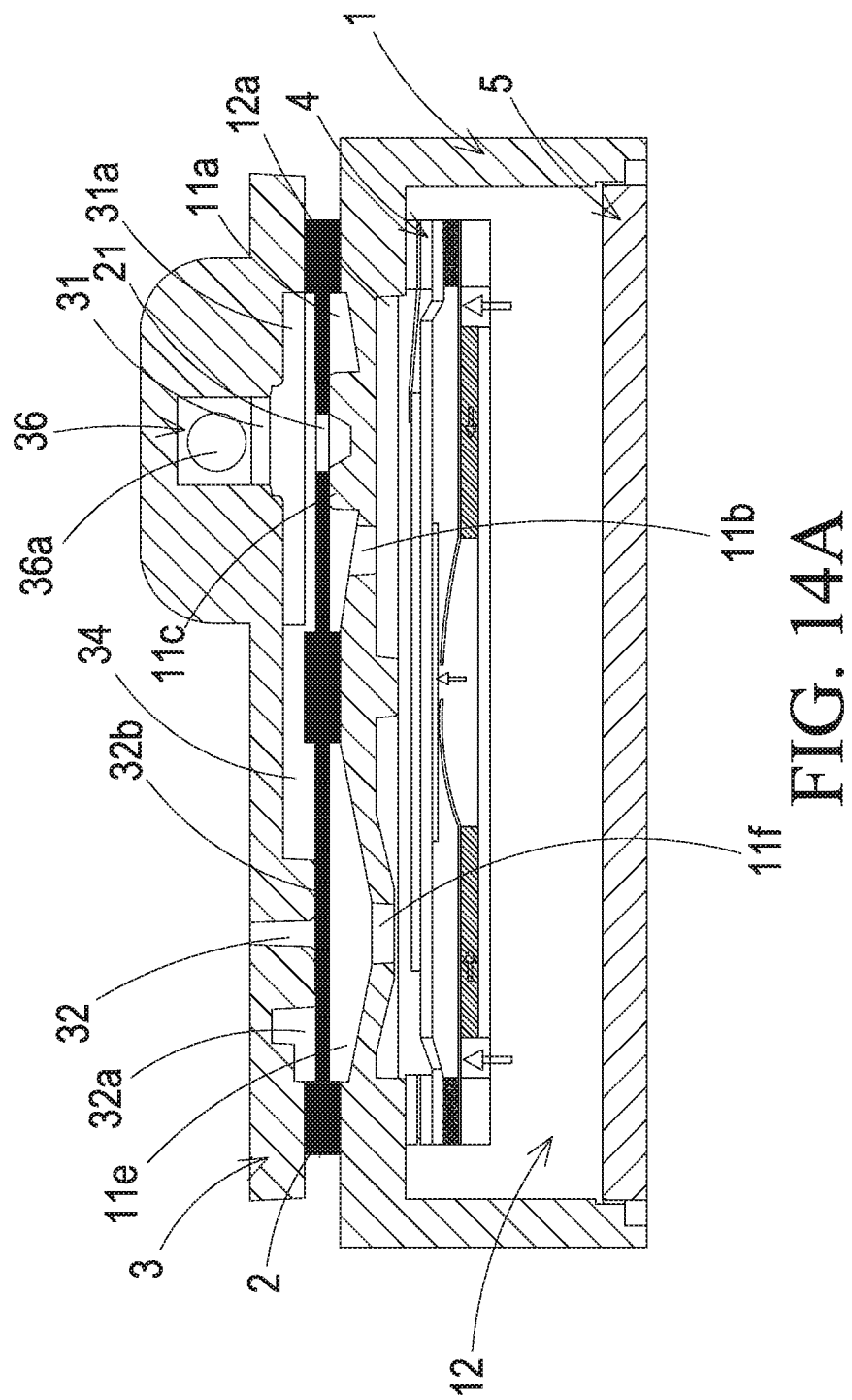
FIG. 14A and FIG. 14B illustrate a schematic gas inflow view of the blood pressure measurement module of the exemplary embodiment.
Figure 14B:
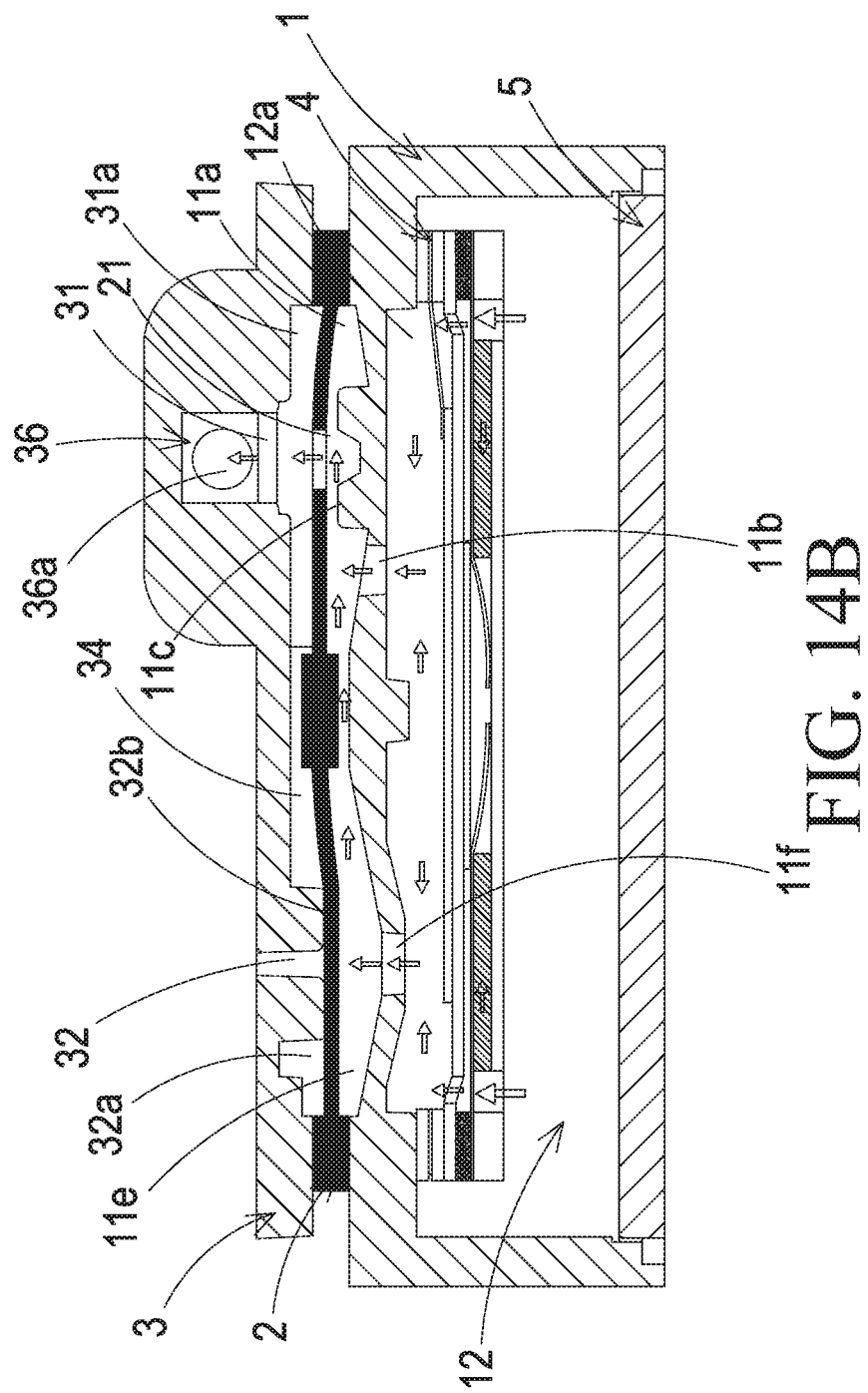

Please refer to FIG. 14A. When the micro pump 4 starts operation, the gas enters into the micro pump 4 from the inlet holes 411 (as shown in FIG. 7A) of the micro pump 4, and the gas is continuously guided to the gas collection chamber 12a. Please refer to FIG. 14B. After the gas is continuously guided to the gas collection chamber 12a, the gas further enters into the first recessed receiving chamber 11a through the first through holes 11b, and then the gas further enters into the second recessed receiving chamber 11e through the second through holes 11f. The gas entering into the first recessed receiving chamber 11a and the second recessed receiving chamber 11e is configured to push the valve plate 2 upwardly, such that the valve plate 2 is moved toward the top cover 3. At the moment, the valve plate 2 abuts against the second protruding structure 32b of the discharge chamber 32a and closes the discharge hole 32. Moreover, the valve plate 2 is detached from the first protruding structure 11c of the first recessed receiving chamber 11a, so that the gas in the first recessed receiving chamber 11a and the second recessed receiving chamber 11e can enter into the inlet chamber 31a through the valve hole 21. And, after the gas enters into the inlet chamber 31a, the gas is guided to the inlet channel 31 and eventually converged in the gas bag 10 (as shown in FIG. 5). In this embodiment, after the gas enters into the inlet channel 31, the gas firstly passes through the common channel 36 and then enters into the gas bag 10 at the connection end 36a, thereby the gas starting to inflate the gas bag 10 to expand the gas bag 10. Hence, the gas bag 10 can be closely attached to the user, and then the pressure sensor 6 can be used to detect the pressure change of the gas bag 10, thereby performing the blood pressure measurement.

Figure 15:
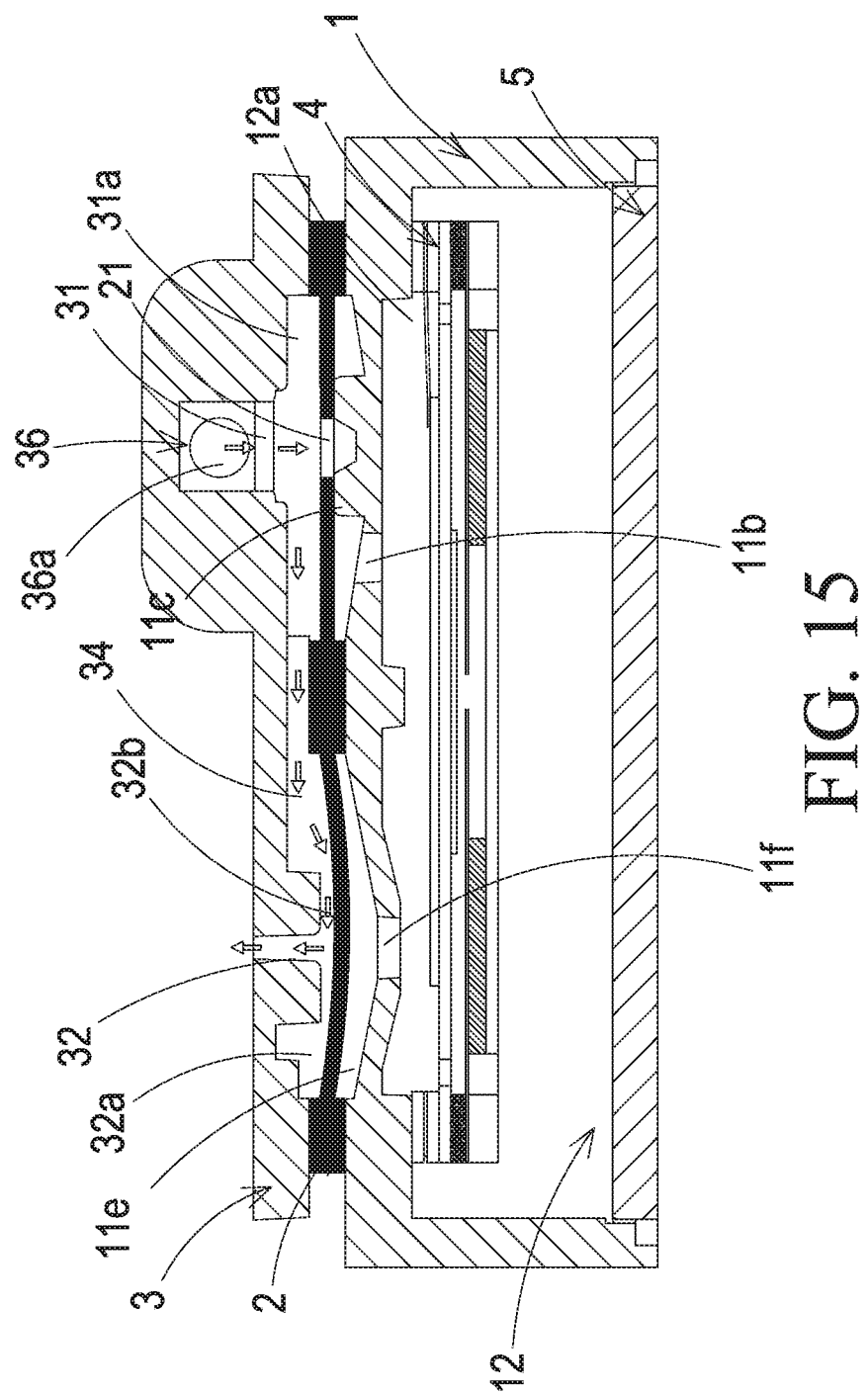
FIG. 15 illustrates a schematic gas discharge view of the blood pressure measurement module of the exemplary embodiment.

As shown in FIG. 15, after the blood pressure measurement is completed, the micro pump 4 stops operation. Hence, the pressure in the gas bag 10 is greater than the pressure in the inlet chamber 31a, and the gas, from the gas bag 10, starts to be guided to the inlet chamber 31a through the inlet channels 31. At the moment the gas is delivered to the inlet chamber 31a, the gas is configured to push[[es]] the valve plate 2 to move downwardly and to allow the valve hole 21 to be closed by the first protruding structure 11c, thereby the gas is allowed to pass through the communication channel 34 and flowing from the inlet chamber 31a to the discharge chamber 32a. Moreover, when the gas pushes the valve plate 2 to move downwardly, the valve plate 2 is detached from the second protruding structure 32b and the valve plate 2 is pushed to fall into the second recessed receiving chamber 11e, so that the discharge chamber 32a can be in communication with the discharge hole 32. Accordingly, after the gas enters into the discharge chamber 32a, the gas can be discharged from the discharge hole 32 to release the gas in the gas bag 10, thereby completing a quick pressure releasing process of the gas bag 10.

Figure 16:
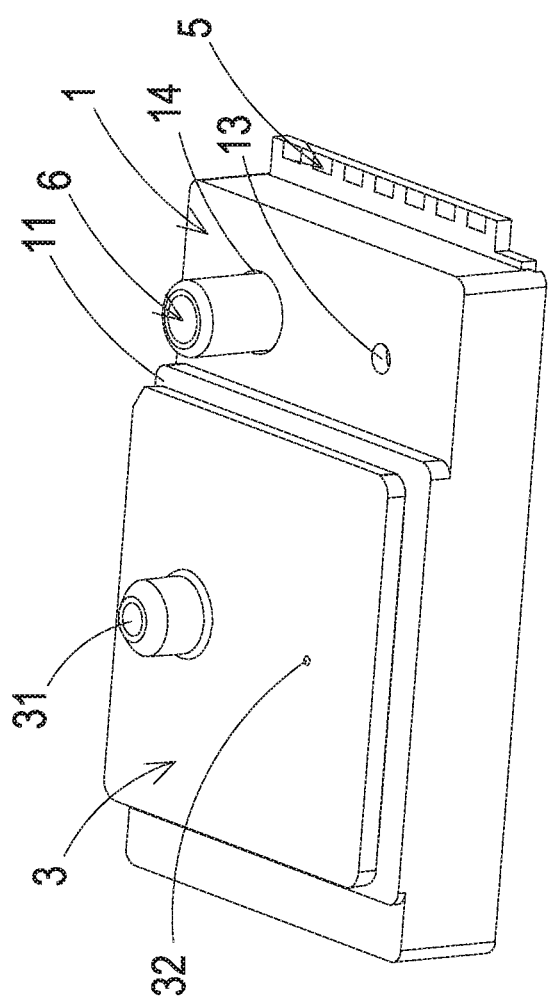
FIG. 16 illustrates a schematic perspective view of a blood pressure measurement module according to another exemplary embodiment of the present disclosure.
Figure 18:
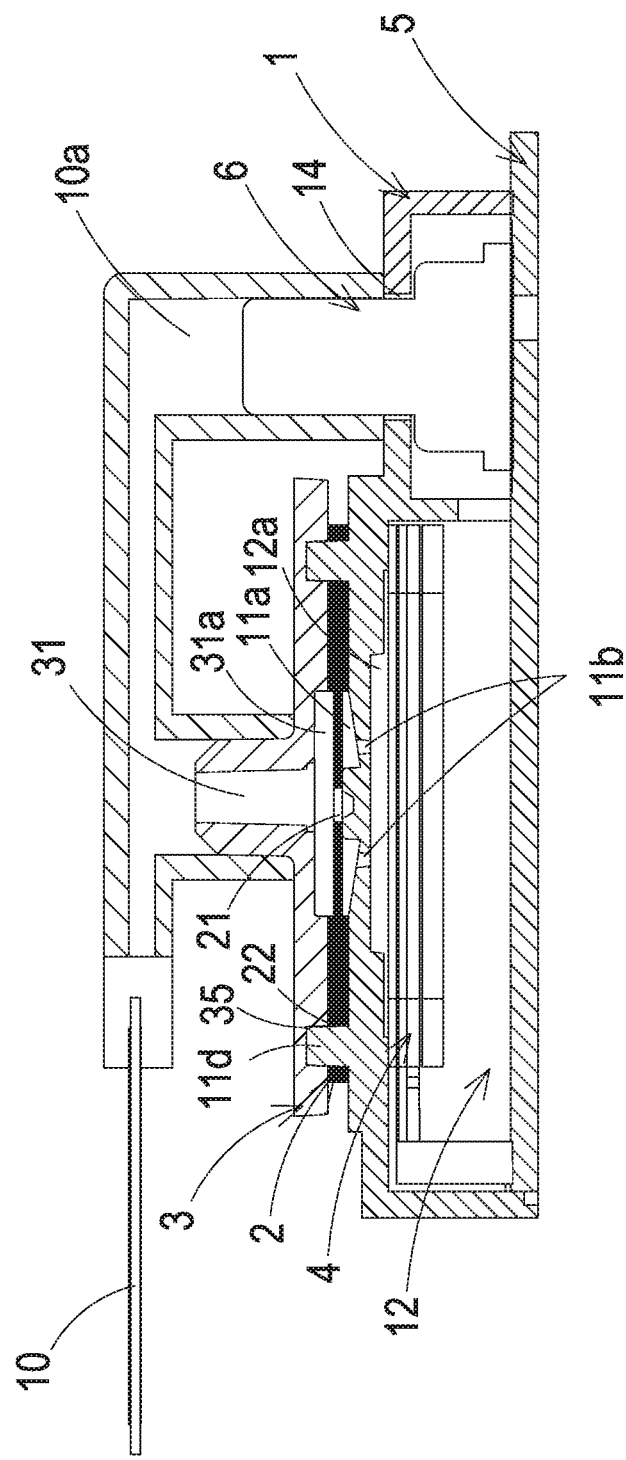
FIG. 18 illustrates a schematic cross-sectional view of the blood pressure measurement module of the another exemplary embodiment.
Figure 19:
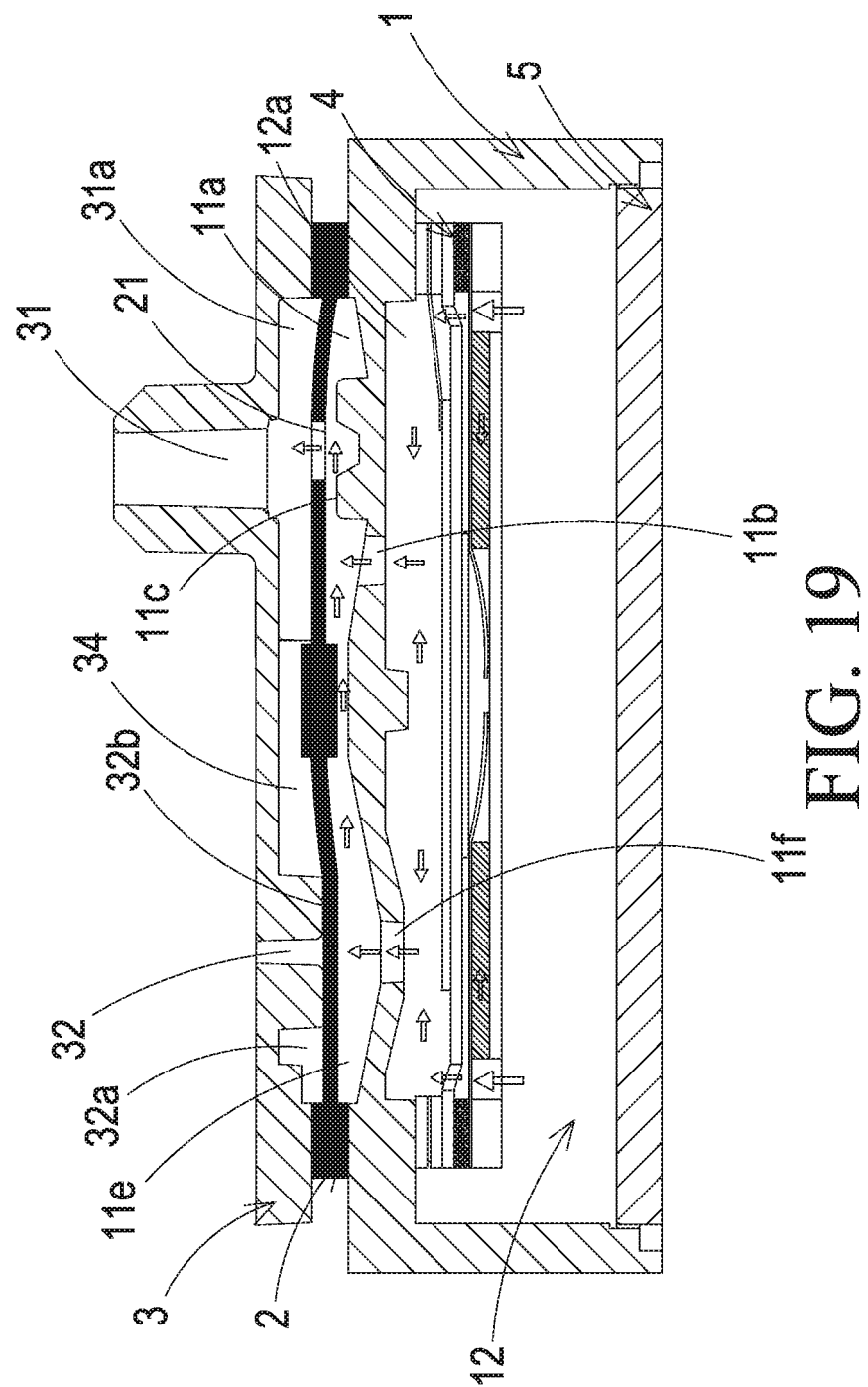
FIG. 19 illustrates a schematic gas inflow view of the blood pressure measurement module of the another exemplary embodiment.
Figure 20:
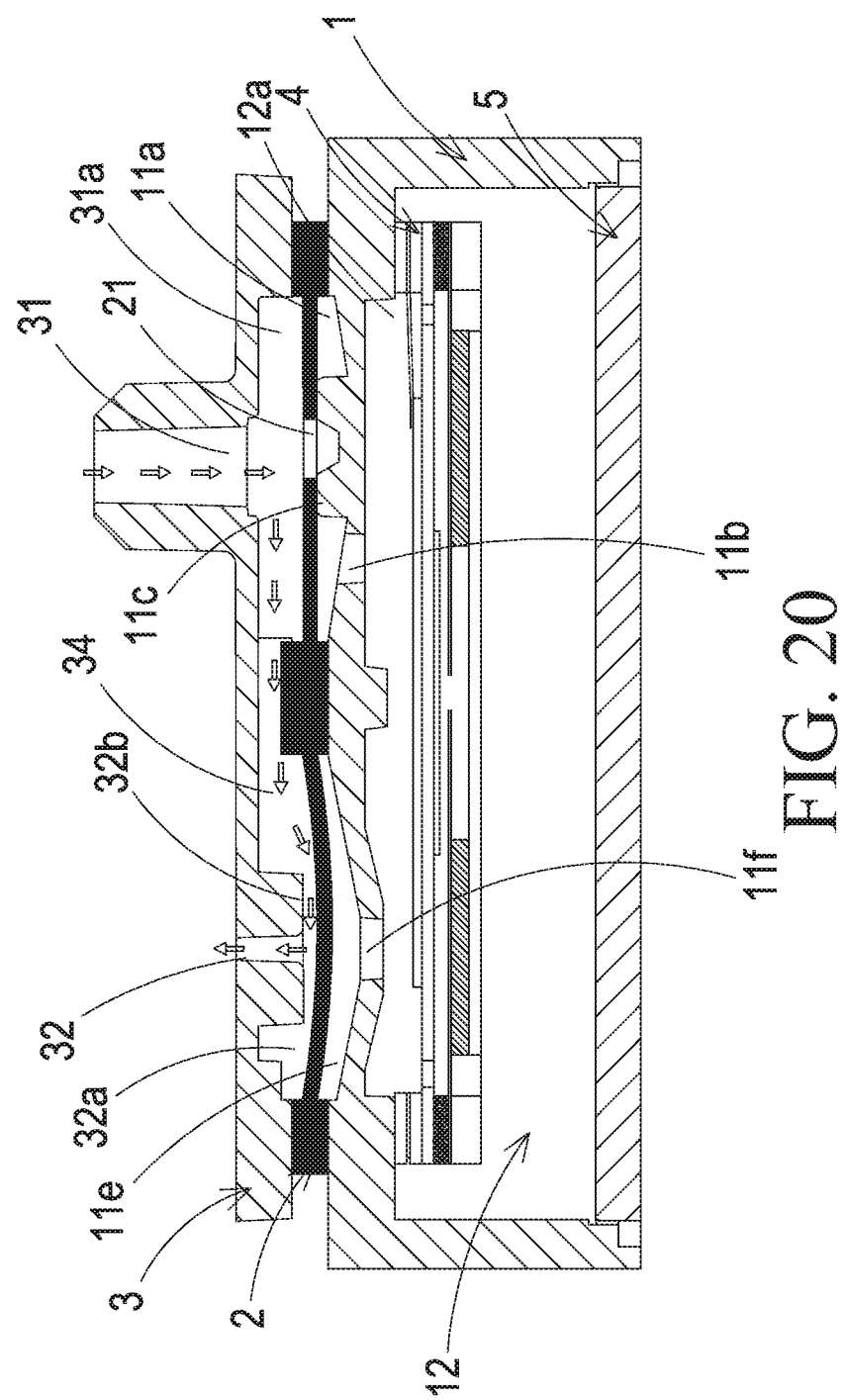
FIG. 20 illustrates a schematic gas discharge view of the blood pressure measurement module of the another exemplary embodiment.

Please refer to FIG. 16. FIG. 16 illustrates another embodiment of the blood pressure measurement module of the present disclosure. Most of the elements in the foregoing embodiment are similar to the corresponding elements in FIG. 16, which are not repeated here. The difference between the foregoing embodiment and the embodiment shown in FIG. 16 is that, in this embodiment, the top cover 3 does not have the common channel 36. Please further refer to FIG. 18. In the embodiment that the top cover 3 does not have the common channel 36, the gas bag 10 has a gas bag duct 10a, and the gas bag duct 10a is in communication with the gas bag 10, and the gas bag duct 10a is further connected to the inlet channel 31 of the top cover 3 and closes the pressure sensor 6. When the micro pump 4 starts operation, the gas enters into the inlet channel 31 (as shown in FIG. 19). After the gas passes through the inlet channel 31, the gas enters into the gas bag 10 through the gas bag duct 10a, thereby inflating the gas bag 10 to press the skin of the user. And, the pressure sensor 6 is used to check the pressure change in the gas bag 10 through the gas bag duct 10a so as to detect the blood pressure of the user. After the measurement is completed, the micro pump 4 stops operation, and the gas is guided back to the inlet channel 31 from the gas bag duct 10a, and the gas is eventually discharged from the discharge hole 32 (as shown in FIG. 20), thereby achieving an effect of quick gas releasing and pressure releasing.

Please refer to FIG. 1 again. In some embodiments, preferably, the length of the blood pressure measurement module of the present disclosure may be between 4 mm and 30 mm, the width of the blood pressure measurement module may be between 2 mm and 16 mm, and the height of the blood pressure measurement module maybe between 1 mm and 8 mm. Therefore, the blood pressure measurement module is suitable for being combined with a portable electronic device. Moreover, in order to be suitable for being combined with a smart watch, preferably, the length of the blood pressure measurement module between 24 mm and 30 mm, the width of the blood pressure measurement module is between 14 mm and 16 mm, and the height of the blood pressure measurement module is between 6 mm and 8 mm.

Figure 21:
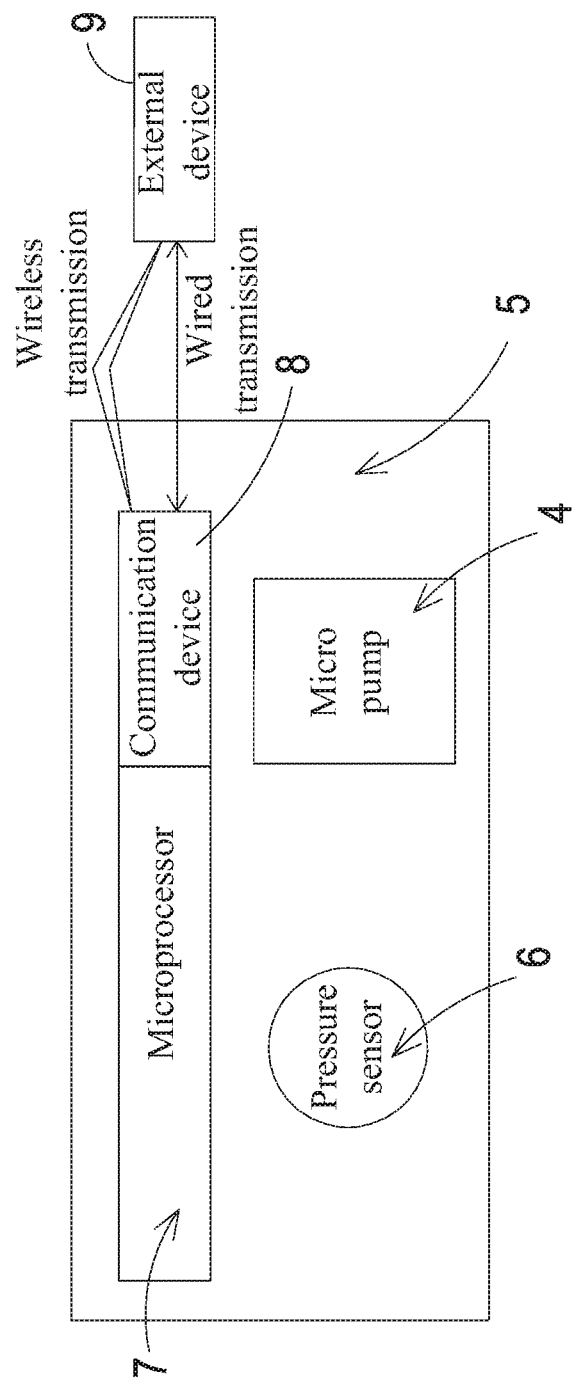
FIG. 21 illustrates a schematic block diagram showing that the blood pressure measure module of the exemplary embodiment is connected to an external device.

Please refer to FIG. 21. The blood pressure measurement module may further include a microprocessor 7 and a communication device 8. The microprocessor 7 and the communication device 8 are disposed on the driving circuit board 5. The microprocessor 7 is configured to receive a measuring signal measured by the pressure sensor 6, to convert the measuring signal into an information data, and to transmit the information data through the communication device 8 to an external device 9 for storing, processing, or applying the information data. The information data can be transmitted to the external device 9 through a wired transmission, a wireless transmission, or both the wired transmission and the wireless transmission. In some embodiments, the external device 9 is at least one device selected from the group consisting of a cloud system, a portable device, and a computer system.

To sum up, one or some embodiments of the present disclosure provides a blood pressure measurement module. With the application of the base, the valve plate, and the top cover, the blood pressure measurement module can inflate or relief the gas bag quickly. Moreover, with the application of the micro pump, the pump size can be greatly reduced, so that the blood pressure measurement module can be suitable for being disposed on a wearable device, such as a smart watch. Thus, the industrial value of the present application is very high, so the application is submitted in accordance with the law.

What is claimed is:
1. A blood pressure measurement module, comprising:
   a base having a valve loading area, an accommodation trough area, a gas inlet hole, and an insertion hole, wherein the valve loading area and the accommodation trough area are respectively disposed on different surfaces of the base, wherein the gas inlet hole and the insertion hole are in communication with the accommodation trough area, wherein a first recessed receiving chamber is disposed on the valve loading area, and a plurality of first through holes penetrate an inner wall of the first recessed receiving chamber, a first protruding structure extends from the first recessed receiving chamber, and wherein an inner wall of the accommodation trough area is recessed to form a gas collection chamber, and the gas collection chamber is in communication with the plurality of first through holes;
   a valve plate disposed and loaded on the valve loading area, wherein the valve plate comprises a valve hole corresponding to the first protruding structure;

a top cover comprising an inlet channel and a discharge hole spaced apart from each other, wherein the top cover has an assembling surface covering the valve plate, wherein a portion of the assembling surface corresponding to the inlet channel is recessed to form an inlet chamber, and the inlet chamber is in communication with the inlet channel, wherein a portion of the assembling surface corresponding to the discharge hole is recessed to form a discharge chamber, and the discharge chamber is in communication with the discharge hole, wherein a communication channel is disposed between the inlet chamber and the discharge chamber, wherein a second protruding structure extends from the discharge chamber, and the discharge hole is opened at a center portion of the second protruding structure, so that the valve plate and the second protruding structure normally abut against each other to form a pre-force action and to close the discharge hole, and wherein the inlet channel is connected to a gas bag for blood pressure measurement;

a micro pump disposed in the accommodation trough area to cover the gas collection chamber;

a driving circuit board covering the accommodation trough area, wherein the driving circuit board is configured to provide a driving signal for the micro pump so as to control an operation of the micro pump; and a pressure sensor disposed on the driving circuit board and electrically connected to the driving circuit board, wherein the pressure sensor is in the insertion hole of the base, and the pressure sensor is connected to the gas bag through the top cover;

wherein the operation of the micro pump is controlled by the driving circuit board for a gas transmission, so that a gas outside the base is guided into the accommodation trough area through the gas inlet hole, and the gas is continuously guided to and converged in the gas collection chamber by the micro pump, so that the gas is configured to push the valve hole of the valve plate and detach the valve hole from the first protruding structure, the gas is allowed to pass through the valve hole so as to be continuously guided into the inlet channel of the top cover and collected in the gas bag, whereby the gas is configured to inflate the gas bag and press skin of a user, so that a blood pressure of the user is allowed to be measured through the pressure sensor.

2. The blood pressure measurement module according to claim 1, wherein the base, the valve plate, the top cover, the micro pump, the driving circuit board, and the pressure sensor are formed as a module structure made of micro-scale materials, and wherein the module structure has a length, a width, and a height.

3. The blood pressure measurement module according to claim 2, wherein the module structure has a size in which the length of the module structure is between 1 μm and 999 μm, the width of the module structure is between 1 μm and 999 μm, and the height of the module structure is between 1 μm and 999 μm.

4. The blood pressure measurement module according to claim 2, wherein the module structure has a size in which the length of the module structure is between 1 nm and 999 nm, the width of the module structure is between 1 nm and 999 nm, and the height of the module structure is between 1 nm and 999 nm.

5. The blood pressure measurement module according to claim 1, wherein the valve loading area of the base further comprises a plurality of protruding posts, the valve plate comprises a plurality of positioning perforations respectively corresponding to the plurality of protruding posts, so that the plurality of positioning perforations are respectively inserted by the protruding posts of the valve loading area, whereby the valve plate is loaded and fixedly positioned on the valve loading area so as to ensure the valve hole to correspond to the first protruding structure.

6. The blood pressure measurement module according to claim 5, wherein the assembling surface of the top cover further comprises a plurality of positioning holes respectively corresponding to the plurality of protruding posts, so that the plurality of positioning holes are respectively inserted by the protruding posts of the valve loading area, whereby the valve plate is loaded on the valve loading area, and the valve plate is fixedly positioned between the base and the top cover.

7. The blood pressure measurement module according to claim 1, wherein the valve loading area of the base further comprises a second recessed receiving chamber, at least one second through hole penetrates an inner wall of the second recessed receiving chamber, and the at least one second through hole is in communication with the gas collection chamber, thereby facilitating the gas to be collected in the gas collection chamber, to pass through the valve hole, and to be guided into the inlet channel of the top cover continuously and collected in the gas bag.

8. The blood pressure measurement module according to claim 7, wherein when the micro pump stops operation, a pressure of the gas collected in the gas bag is greater than a pressure of the gas converged in the gas collection chamber, so that the gas collected in the gas bag is guided out from the gas channel and pushes the valve hole of the valve plate, wherein the valve hole is maintained in contact with the first protruding structure so as to close the valve hole, the gas passes through the communication channel and is guided into the discharge chamber, and the gas is configured to push the valve plate and detach the valve plate from the second protruding structure so as to open the discharge hole, and allow the gas collected in the gas bag to be discharged out of the top cover through the discharge hole, thereby completing a quick pressure releasing process of the gas bag.

9. The blood pressure measurement module according to claim 8, wherein when the quick pressure releasing process of the gas bag is executed, the valve plate is pushed to fall into the second recessed receiving chamber, so that a distance between the valve plate and the second protruding structure increases so as to open the discharge hole after the valve plate is detached from the second protruding structure.

10. The blood pressure measurement module according to claim 1, wherein the top cover comprises a common channel being integrated with and in communication with the inlet channel, and the common channel extends to cover the pressure sensor, wherein the common channel has a connection end for connecting to the gas bag, whereby the pressure sensor is in communication with the gas bag through the common channel so as to perform gas pressure detection.

11. The blood pressure measurement module according to claim 1, further comprising a microprocessor and a communication device, wherein the microprocessor and the communication device are disposed on the driving circuit board, and the microprocessor is configured to receive a measuring signal measured by the pressure sensor, to convert the measuring signal into an information data set, and to transmit the information data through the communication device to an external device for storing, processing, or applying the information data.

12. The blood pressure measurement module according to claim 11, wherein the information data is transmitted to the external device through a wired transmission, or a wireless transmission, or both the wired transmission and the wireless transmission.

13. The blood pressure measurement module according to claim 11, wherein the external device is at least one selected from a group consisting of a cloud system, a portable device, and a computer system.

14. The blood pressure measurement module according to claim 1, wherein the micro pump comprises:
   an inlet plate having at least one inlet hole, at least one convergence channel corresponding to the at least one inlet hole, and a convergence chamber, wherein the at least one inlet hole is configured to guide the gas outside the micro pump to flow therein, and the at least one convergence channel is configured to guide the gas from the at least one inlet hole to be converged at the convergence chamber;
   a resonance sheet having a perforation corresponding to the convergence chamber, wherein a periphery of the perforation is a movable portion; and
   a piezoelectric actuator disposed correspondingly to the resonance sheet;
   a first insulation sheet;
   a conductive sheet; and
   a second insulation sheet;
   wherein the inlet plate, the resonance sheet, the piezoelectric actuator, the first insulation sheet, the conductive sheet, and the second insulation sheet are arranged sequentially and stacked with each other, wherein a chamber space is formed between the resonance sheet and the piezoelectric actuator, so that when the piezoelectric actuator is driven, the gas outside the micro pump is guided into the micro pump through the at least one inlet hole of the inlet plate, is converged at the convergence chamber via the at least one convergence channel, and flows through the perforation of the resonance sheet by a resonance effect between the piezoelectric actuator and the movable portion of the resonance sheet.

15. The blood pressure measurement module according to claim 14, wherein the piezoelectric actuator comprises:
   a suspension plate having a square shape, wherein the suspension plate is capable of bending and vibrating;
   an outer frame disposed around a periphery of the suspension plate;
   at least one supporting element connected between the suspension plate and the outer frame to provide a flexible support for the suspension plate; and
   a piezoelectric element having a side length, wherein the side length of the piezoelectric element is smaller than or equal to a side length of the suspension plate, and the piezoelectric element is attached to a surface of the suspension plate so as to drive the suspension plate to bend and vibrate when the piezoelectric element is applied with a voltage.

16. The blood pressure measurement module according to claim 14, wherein the piezoelectric actuator comprises:
   a suspension plate having a square shape, wherein the suspension plate is capable of bending and vibrating;
   an outer frame disposed around a periphery of the suspension plate;
   at least one supporting element connected between the suspension plate and the outer frame to provide a flexible support for the suspension plate, and a surface of the suspension plate and a surface of the outer frame are not planar, wherein a chamber gap is maintained between the surface of the suspension plate and the resonance sheet; and
   a piezoelectric element having a side length, wherein the side length of the piezoelectric element is smaller than or equal to a side length of the suspension plate, and the piezoelectric element is attached to a surface of the suspension plate so as to apply a voltage to the suspension plate to drive the suspension plate to bend and vibrate.

17. The blood pressure measurement module according to claim 1, wherein the micro pump is a micro-electromechanical systems (MEMS) pump and comprises:
   a first substrate having a plurality of ventilation holes, wherein each of the plurality of ventilation holes is a conical hole;
   a first oxide layer stacked on the first substrate, wherein the first oxide layer has a plurality of convergence troughs and a convergence chamber, wherein the plurality of convergence troughs is in communication between the convergence chamber and the plurality of ventilation holes;
   a second substrate combined with the first substrate, comprising:
   a silicon wafer layer, having:
   an actuation portion having a circular shape;
   an outer peripheral portion having a hollow ring shape and surrounding a periphery of the actuation portion;
   a plurality of connection portions respectively connected between the actuation portion and the outer peripheral portion; and
   a plurality of fluid channels surrounding the periphery of the actuation portion and located between the plurality of connection portions;
   a second oxide layer formed on the silicon wafer layer, wherein the second oxide layer has a hollow ring shape, and the second oxide layer and the silicon wafer layer together define a vibration chamber; and
   a silicon material layer having a circular shape and located at the second oxide layer, wherein the silicon material layer is combined with the first oxide layer, and the silicon material layer has:
   a third through hole located at a center portion of the silicon material layer;
   a vibration portion located at a peripheral area of the third through hole;
   a fixed portion located at a peripheral area of the silicon material layer; and
   a piezoelectric component having a circular shape and stacked on the actuation portion of the silicon wafer layer.

18. The blood pressure measurement module according to claim 17, wherein the piezoelectric element comprises:
   a lower electrode layer;
   a piezoelectric layer stacked on the lower electrode layer;
   an insulation layer disposed on a part of a surface of the piezoelectric layer and a part of a surface of the lower electrode layer; and
   an upper electrode layer stacked on the insulation layer and a remaining portion of the surface of the piezoelectric layer where the insulation layer is not disposed, wherein the upper electrode layer is used for electrically connecting to the piezoelectric layer.

19. The blood pressure measurement module according to claim 1, wherein a length of the blood pressure measurement module is between 4 mm and 30 mm, a width of the blood pressure measurement module is between 2 mm and 16 mm, and a height of the blood pressure measurement module is between 1 mm and 8 mm.

20. The blood pressure measurement module according to claim 19, wherein a length of the blood pressure measurement module is between 24 mm and 30 mm, a width of the blood pressure measurement module is between 14 mm and 16 mm, and a height of the blood pressure measurement module is between 6 mm and 8 mm.

* * * * *